US012560793B2

(12) United States Patent
Valdes et al.

(10) Patent No.: US 12,560,793 B2
(45) Date of Patent: *Feb. 24, 2026

(54) METHOD AND APPARATUS FOR QUANTITATIVE HYPERSPECTRAL FLUORESCENCE AND REFLECTANCE IMAGING FOR SURGICAL GUIDANCE

(71) Applicant: THE TRUSTEES OF DARTMOUTH COLLEGE, Hanover, NH (US)

(72) Inventors: Pablo A. Valdes, Hanover, NH (US); David W. Roberts, Lyme, NH (US); Keith D. Paulsen, Hanover, NH (US); Frederic Leblond, Montreal (CA)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/783,802

(22) Filed: Jul. 25, 2024

(65) Prior Publication Data

US 2024/0377627 A1     Nov. 14, 2024

Related U.S. Application Data

(63) Continuation of application No. 18/144,767, filed on May 8, 2023, now Pat. No. 12,061,328, which is a
(Continued)

(51) Int. Cl.
G02B 21/06        (2006.01)
A61B 1/06         (2006.01)
G02B 21/36        (2006.01)

(52) U.S. Cl.
CPC ............. G02B 21/06 (2013.01); A61B 1/063 (2013.01); G02B 21/36 (2013.01)

(58) Field of Classification Search
None
See application file for complete search history.

(56) References Cited

U.S. PATENT DOCUMENTS

| | | | |
|---|---|---|---|
| 5,109,276 A | 4/1992 | Nudelman et al. | |
| 5,303,705 A | 4/1994 | Nenov | |
| | (Continued) | | |

FOREIGN PATENT DOCUMENTS

| | | |
|---|---|---|
| JP | 2006195240 A | 7/2006 |
| KR | 20110097030 A | 8/2011 |
| | (Continued) | |

OTHER PUBLICATIONS

Bradley et al., "A review of attenuation correction techniques for tissue fluorescence", Journal of the Royal Society Interface, vol. 3, Issue 6, Feb. 22, 2006, pp. 1-13.
(Continued)

*Primary Examiner* — Katherine L Fernandez
(74) *Attorney, Agent, or Firm* — Cozen O'Connor

(57) ABSTRACT

A surgical microscope with a fluorescence excitation illuminator receives fluorescence emissions from a target, the surgical microscope having an optical output port. A tunable filter passes a filtered portion of light from the surgical microscope, the filtered light has wavelengths selected by the tunable filter and is provided to a high-resolution, broad-bandwidth electronic camera. The electronic camera converts light from the tunable filter to electrical signals. A processor processes the electrical signals to form an image of the target including estimated fluorophore depth, the image corrected for optical absorption and scattering parameters of the target. The processor also performs deformation modeling of the target to track tumor position changes during surgery. Embodiments track surface changes of the target using stereo cameras to support the deformation modeling, some images may include information from pre-
(Continued)

operative CT or MRI, and some images may map biomarkers like HbO2 and DexoHb.

22 Claims, 11 Drawing Sheets

Related U.S. Application Data continuation of application No. 16/443,760, filed on Jun. 17, 2019, now Pat. No. 11,656,448, which is a continuation of application No. 14/373,443, filed as application No. PCT/US2013/022266 on Jan. 18, 2013, now abandoned.

(60) Provisional application No. 61/588,708, filed on Jan. 20, 2012.

(56) References Cited

U.S. PATENT DOCUMENTS

| | | | |
|---|---|---|---|
| 5,381,236 A | 1/1995 | Morgan | |
| 5,793,350 A | 8/1998 | Chandavarkar et al. | |
| 5,810,731 A | 9/1998 | Sarvazyan et al. | |
| 6,175,759 B1 | 1/2001 | Chan et al. | |
| 6,208,886 B1 | 3/2001 | Alfano et al. | |
| 6,379,302 B1 | 4/2002 | Kessman et al. | |
| 6,661,571 B1 | 12/2003 | Shioda et al. | |
| 6,678,398 B2 | 1/2004 | Wolters et al. | |
| 6,793,350 B1 | 9/2004 | Raskar et al. | |
| 6,961,405 B2 | 11/2005 | Scherch | |
| 7,085,400 B1 | 8/2006 | Holsing et al. | |
| 7,387,802 B2 | 6/2008 | Sambanthamurthi et al. | |
| 7,804,075 B2 | 9/2010 | Ntziachristos et al. | |
| 7,945,077 B2 | 5/2011 | Demos | |
| 8,406,859 B2 | 3/2013 | Zuzak et al. | |
| 8,408,569 B2 | 4/2013 | Keil et al. | |
| 8,948,851 B2 | 2/2015 | Leblond et al. | |
| 9,052,384 B2 | 6/2015 | Hartov et al. | |
| 9,167,222 B2 | 10/2015 | Park et al. | |
| 9,330,477 B2 | 5/2016 | Rappel | |
| 9,336,592 B2 | 5/2016 | Fan et al. | |
| 9,456,200 B2 | 9/2016 | Ji et al. | |
| 9,649,502 B2 | 5/2017 | Phillips et al. | |
| 9,655,545 B2 | 5/2017 | Ji et al. | |
| 9,699,438 B2 | 7/2017 | Walsh | |
| 9,712,746 B2 | 7/2017 | Arcas et al. | |
| 9,766,441 B2 | 9/2017 | Rappel | |
| 10,357,654 B1 | 7/2019 | Pilly et al. | |
| 10,568,535 B2 | 2/2020 | Roberts et al. | |
| 11,083,401 B2 | 8/2021 | Sridhar et al. | |
| 11,164,371 B2 | 11/2021 | Yellin et al. | |
| 11,311,724 B2 | 4/2022 | Lerman et al. | |
| 12,061,328 B2 | 8/2024 | Valdes et al. | |
| 12,390,122 B2 | 8/2025 | Navarro De Lara et al. | |
| 2002/0080481 A1 | 6/2002 | Tachihara et al. | |
| 2002/0099295 A1 | 7/2002 | Gil et al. | |
| 2003/0158470 A1 | 8/2003 | Wolters et al. | |
| 2004/0010192 A1 | 1/2004 | Benaron et al. | |
| 2004/0015062 A1 | 1/2004 | Ntziachristos et al. | |
| 2004/0215072 A1 | 10/2004 | Zhu | |
| 2005/0085732 A1 | 4/2005 | Sevick-muraca et al. | |
| 2005/0111758 A1 | 5/2005 | Lange et al. | |
| 2005/0215911 A1 | 9/2005 | Alfano et al. | |
| 2006/0024390 A1 | 2/2006 | Schauss et al. | |
| 2006/0033026 A1 | 2/2006 | Treado et al. | |
| 2006/0118742 A1 | 6/2006 | Levenson et al. | |
| 2007/0038126 A1 | 2/2007 | Pyle et al. | |
| 2007/0083124 A1 | 4/2007 | Ehben et al. | |
| 2007/0145136 A1 | 6/2007 | Wikiof et al. | |
| 2007/0165927 A1 | 7/2007 | Muradyan et al. | |
| 2007/0167835 A1 | 7/2007 | Yu et al. | |
| 2007/0236414 A1 | 10/2007 | Lin | |
| 2007/0236514 A1 | 10/2007 | Agusanto et al. | |
| 2007/0238957 A1 | 10/2007 | Yared | |
| 2007/0299335 A1 | 12/2007 | Declerck et al. | |
| 2008/0218727 A1 | 9/2008 | Djeziri et al. | |
| 2008/0267472 A1 | 10/2008 | Demos | |
| 2008/0272312 A1 | 11/2008 | Tuschel | |
| 2009/0021746 A1 | 1/2009 | Toida et al. | |
| 2009/0036902 A1 | 2/2009 | Dimaio et al. | |
| 2009/0076732 A1 | 3/2009 | Sprigle et al. | |
| 2009/0137908 A1 | 5/2009 | Patwardhan | |
| 2009/0180178 A1 | 7/2009 | Luecke et al. | |
| 2009/0295910 A1 | 12/2009 | Mir et al. | |
| 2009/0312611 A1 | 12/2009 | Mangiardi | |
| 2009/0326362 A1 | 12/2009 | Carlse et al. | |
| 2010/0019170 A1 | 1/2010 | Marini et al. | |
| 2010/0056928 A1 | 3/2010 | Zuzak et al. | |
| 2010/0085423 A1 | 4/2010 | Lange | |
| 2010/0106013 A1 | 4/2010 | Morishita | |
| 2010/0145416 A1 | 6/2010 | Kang et al. | |
| 2010/0201789 A1 | 8/2010 | Yahagi | |
| 2010/0208963 A1 | 8/2010 | Kruecker et al. | |
| 2010/0231593 A1 | 9/2010 | Zhou et al. | |
| 2011/0054355 A1 | 3/2011 | Hunter et al. | |
| 2011/0102549 A1 | 5/2011 | Takahashi | |
| 2011/0128352 A1 | 6/2011 | Higgins et al. | |
| 2011/0175910 A1 | 7/2011 | Yahagi | |
| 2011/0183370 A1 | 7/2011 | Noiseux et al. | |
| 2011/0222757 A1 | 9/2011 | Yeatman et al. | |
| 2011/0275932 A1* | 11/2011 | Leblond | A61B 5/0062 |
| | | | 600/425 |
| 2011/0293142 A1 | 12/2011 | Van et al. | |
| 2012/0002012 A1 | 1/2012 | Ogrady et al. | |
| 2012/0112098 A1 | 5/2012 | Hoyt | |
| 2012/0133740 A1 | 5/2012 | Klimov et al. | |
| 2012/0307056 A1 | 12/2012 | Zuzak et al. | |
| 2012/0307081 A1 | 12/2012 | Dewald et al. | |
| 2013/0012794 A1 | 1/2013 | Zeng et al. | |
| 2013/0038689 A1 | 2/2013 | Mcdowall | |
| 2013/0076863 A1 | 3/2013 | Rappel | |
| 2013/0259805 A1 | 10/2013 | Bacskai | |
| 2014/0020476 A1 | 1/2014 | Inoue et al. | |
| 2014/0063241 A1 | 3/2014 | Li et al. | |
| 2014/0362186 A1 | 12/2014 | Ji et al. | |
| 2014/0378843 A1 | 12/2014 | Valdes et al. | |
| 2015/0264340 A1 | 9/2015 | Seidl et al. | |
| 2015/0374308 A1 | 12/2015 | Tichauer et al. | |
| 2016/0278678 A1 | 9/2016 | Valdes et al. | |
| 2017/0119330 A1 | 5/2017 | Tichauer et al. | |

FOREIGN PATENT DOCUMENTS

| | | | |
|---|---|---|---|
| KR | 101088364 B1 | 12/2011 | |
| WO | 0027131 A2 | 5/2000 | |
| WO | 2005089637 A2 | 9/2005 | |
| WO | 2005099581 A1 | 10/2005 | |
| WO | 2007111570 A2 | 10/2007 | |
| WO | 2009061425 A1 | 5/2009 | |
| WO | 2009143491 A2 | 11/2009 | |
| WO | 2010090673 A1 | 8/2010 | |
| WO | 2011113162 A1 | 9/2011 | |
| WO | 2013040555 A2 | 3/2013 | |
| WO | 2013103870 A1 | 7/2013 | |
| WO | 2013109966 A1 | 7/2013 | |
| WO | 2013116694 A1 | 8/2013 | |
| WO | 2013122710 A1 | 8/2013 | |
| WO | 2014127145 A1 | 8/2014 | |
| WO | 2015023990 A1 | 2/2015 | |
| WO | 2015187620 A1 | 12/2015 | |
| WO | 2016007734 A1 | 1/2016 | |

OTHER PUBLICATIONS

Davis et al. (2005) "Contrast-detail analysis characterizing diffuse optical fluorescence tomography image reconstruction," J. Biomed. Optics, vol. 10(5):050501, pp. 1-3.

Diop et al. (2012) "Deconvolution method for recovering the photon time-of-flight distribution from time-resolved measurements," Optics Letters, vol. 37, pp. 2358-2360.

(56)  References Cited

OTHER PUBLICATIONS

Fan (May 2012) "Later Stage Brain Deformation Compensation In Image-Guided Neurosurgery," Ph.D. Dissertation, Dartmouth College.
Fan et al. (2012) "Registering Stereovision Surface with Preoperative Magnetic Resonance Images for Brain Shift compensation," Proceedings vol. 8316, Medical Imaging 2012: Image-Guided Procedures, Robotic Interventions, and Modeling, 83161C, pp. 1-10.
Fan et al. (Mar. 2, 2011) "Simulation of brain tumor resection in image-guided neurosurgery," Medical Imaging, Proc. of SPIE., vol. 7964:79640U, pp. 1-11.
Fellers et al. (2012) "Acousto-Optic Tunable Filters (AOTFs)," Accessible on the Internet at URL: http://www.olympusmicro.com/primer/techniques/confocal/aolfintro.html. [Last Accessed Oct. 12, 2017].
Feng et al. (2010) "Relative Brain Displacement and Deformation During Constrained Mild Frontal Head Impact," J R Soc Interface. 7(53):1677-88.
Final Office Action for U.S. Appl. No. 15/367,243, mailed Mar. 25, 2019, 11 pages.
Final Rejection in U.S. Appl. No. 14/373,443 mailed on Jun. 21, 2017, 20 pp.
Friesen et al. (2002) "5-Aminolevulinic acid-based photodynamic detection and therapy of brain tumors (review)," Int. J. Oncol., vol. 21(3), pp. 577-582.
Gao et al. (2010) "Snapshot Image Mapping Spectrometer (IMS) with high sampling density for hyperspectral microscopy," Optics Express. 18:14330-14344.
Hartov et al. (1999) "Error Analysis for a Free-Hand Three Dimensional Ultrasound System for Neuronavigation," Neurosurg. Focus. 6(3):5. 14 pgs.
Hillman (2007) "Optical brain imaging in vivo: techniques and applications from animal to man," J. Biomed. Optics, vol. 12(5):051402.
International Search Report and Written Opinion dated Oct. 7, 2015, for International Application No. PCT/US2015/039728 (11 pages).
International Search Report and Written Opinion for PCT/US2009/045082 dated Jan. 7, 2010, 10 pages.
International Search Report and Written Opinion for PCT/US2012/055755 dated Feb. 28, 2013, 7 pages.
International Search Report with Written Opinion corresponding to International Patent Application No. PCT/US2009/066839, mailed Jun. 25, 2010.
International Search Report with Written Opinion corresponding to International Patent Application No. PCT/US2013/020352, mailed Apr. 26, 2013.
International Search Report with Written Opinion corresponding to International Patent Application No. PCT/US2013/022266, mailed May 15, 2013.
International Search Report with Written Opinion corresponding to International Patent Application No. PCT/US2013/024400, mailed May 15, 2013.
International Search Report with Written Opinion corresponding to International Patent Application No. PCT/US2014/016291, mailed May 27, 2014.
International Search Report with Written Opinion corresponding to International Patent Application No. PCT/US2014/051356, mailed Dec. 9, 2014.
International Search Report with Written Opinion corresponding to International Patent Application No. PCT/US2015/033672, mailed Aug. 19, 2015.
Joshi et al. (2010) "DigiWarp: a method for deformable mouse atlas warping to surface topographic data," Phys. Med. Biol. 55(20):6197-6214.
Kuroiwa et al., "Development of a Fluorescein Operative Microscope for Use During Malignant Glioma Surgery a Technical Note and Preliminary Report," Surg. Neurol. (1998), vol. 50(1), pp. 41-49.
Leblond et al. (2007) "Diffuse optical fluorescence tomography using lime-resolved data acquired transmission," Proceedings vol. 6431, Multimodal Biomedical Imaging II. 643106.

Miller et al., "Mechanical Properties of Brain Tissue In-Vivo: Experiment and Computer Simulation," Journal of Biomechanics (2000), vol. 33, pp. 1369-1376.
Najib et al. (Apr. 2011) "Transcranial Brain Stimulation: Clinical Applications and Future Directions," Neurosurg. Clin. N. Am. 22(2):233-251.
Non Final Office Action for U.S. Appl. No. 15/044,097, mailed Apr. 19, 2019, 19 pages.
Non Final Office Action for U.S. Appl. No. 15/367,243, mailed Sep. 10, 2018, 14 pages.
Non Final Office Action for U.S. Appl. No. 16/443,760, mailed Feb. 16, 2022, 18 pages.
Non Final Office Action for U.S. Appl. No. 12/994,044, mailed Jan. 3, 2014, 11 pgs.
Non Final Office Action for U.S. Appl. No. 12/994,044, mailed Oct. 6, 2014, 15 pgs.
Non Final Office Action for U.S. Appl. No. 14/345,029, mailed Jul. 25, 2016, 10 pgs.
Non Final Office Action for U.S. Appl. No. 14/345,029, mailed Oct. 7, 2015, 10 pgs.
Non-Final Office Action for U.S. Appl. No. 14/767,836 dated Jan. 10, 2019, 17 pages.
Notice of Allowance corresponding to U.S. Appl. No. 12/994,044, mailed Feb. 5, 2015, 11 pgs.
Notice of Allowance corresponding to U.S. Appl. No. 13/145,505, mailed Sep. 30, 2014.
Notice of Allowance corresponding to U.S. Appl. No. 14/345,029, mailed Feb. 14, 2017, 9 pgs.
Notice of Allowance corresponding to U.S. Appl. No. 14/370,713, mailed May 18, 2016.
Notice of Allowance corresponding to U.S. Appl. No. 14/375,311, mailed Jan. 20, 2016.
Notice of Allowance for U.S. Appl. No. 15/367,243, mailed Oct. 21, 2019, 7 pages.
Nourrit et al., "High-resolution hyperspectral imaging of the retina with a modified fundus camera," J. Fr. Opthamol. (2010), vol. 33(10), pp. 686-692.
Ntziachristos et al. (2000) "Concurrent MRI and diffuse optical tomography of breast after indocyanine green enhancement," Proc. Nall. Acad. Sci. USA. 97(6):2767-72.
Ntziachristos et al. (2002) "Charge-coupled-device based scanner for tomography of fluorescent near-infrared robes in turbid media," Medical Physics, vol. 29(5), pp. 803-809.
Office Action corresponding to U.S. Appl. No. 12/994,044, mailed May 15, 2014, 13 pgs.
Office Action corresponding to U.S. Appl. No. 13/145,505, mailed Jun. 20, 2013.
Office Action corresponding to U.S. Appl. No. 13/145,505, mailed Nov. 14, 2013, 10 pgs.
Office Action corresponding to U.S. Appl. No. 14/370,713, mailed Feb. 2, 2016.
Patwardhan (2005) "Monte Carlo Simulation of Light-Tissue Interaction: Three-Dimensional Simulation for Trans-Ilumination-Based Imaging of Skin Lesions," IEEE Transactions on Biomedical Engineering. 52(7):1227-1236.
Rajaram et al. (2008), "Lookup table-based inverse model for determining optical properties of turbid media" J Biomed Opt. 2008; 13(5): 050501.
Raymond et al. (2010) "Lifetime-based tomographic multiplexing," Journal of Biomedical Optics, vol. 15, Issue 4, 9 pp.
Restriction Requirement corresponding to U.S. Appl. No. 12/994,044, mailed Oct. 21, 2013, 5 pgs.
Restriction Requirement corresponding to U.S. Appl. No. 13/145,505, mailed Mar. 27, 2015, 9 pgs.
Restriction Requirement corresponding to U.S. Appl. No. 14/373,443, mailed Sep. 8, 2016, 10 pgs.
Restriction Requirement corresponding to U.S. Appl. No. 14/375,311, mailed Oct. 5, 2015, 6 pgs.
Restriction Requirement for U.S. Appl. No. 14/767,836, mailed Jun. 15, 2018, 10 pages.

(56)     References Cited

OTHER PUBLICATIONS

Saager et al., "Quantitative fluorescence imaging of protoporphyrin IX through determination of tissue optical properties in the spatial frequency domain", Journal of Biomedical Optics, Dec. 2011, vol. 16, Issue 12, pp. 1-5.

Sabet et al. (2008) "Deformation of the human brain induced by mild angular head acceleration," J. Biomech., vol. 41, pp. 307-315.

Stummer et al. (2006) "Fluorescence-guided surgery with 5-aminolevulinic acid for resection of malignant glioma: a randomised controlled multicentre phase III trial," Lancet Oncology, vol. 7, pp. 392-401.

SUN (May 2004) "Stereopsis-Guided Brain Shill Compensation," Ph. D. Dissertation. Dartmouth College.

Sun et al. (2005) "Stereopsis-guided brain shift compensation," IEEE Trans. Med. Imaging., vol. 24(8), pp. 1039-1052.

Swartling et al. (2005) "Fluorescence spectra provide information on the depth of fluorescent lesions in tissue," Optics Letters. 44(10):1934-1941.

Tichauer et al. (Apr. 2014), "Accounting for pharmacokinetic differences in dual-tracer receptor density imaging", Phys. Med. Biol. 59 (2014)2341-2351.

Tichauer et al. (Jan. 2013), "Dual-tracer background subtraction approach for fluorescent molecular tomography." Journal of Biomedical Optics, vol. 18(1 ), 016003.

Tichauer et al., "Improved tumor contrast achieved single time point dual-reporter fluorescence imaging", Journal of Biomedical Optics, 17(6), 066001, Jun. 2012.

U.S. Appl. No. 14/373,443, Final Office Action mailed Dec. 17, 2018, 26 pp.

U.S. Appl. No. 14/373,443, Non-Final Rejection dated Mar. 9, 2018; 20 pp.

U.S. Appl. No. 14/373,443; Office Action dated Nov. 16, 2016 (17 pgs).

Valdes et al. (2011) "Quantitative fluorescence in intracranial tumor: implications for ALA-induced PplX as an Intraoperative biomarker," J. Neurosurg., vol. 115, pp. 11-17.

Valdes et al. (Jun. 1, 2012) "A spectrally constrained dual-band normalization technique for protoporphyrin IX Quantification in fluorescence-guided surgery," Optics Letters. 37(11):1817-1819.

Vigneron et al. (2009) "2D XFEM-Based Modeling of Retration and Successive Resections for Preoperative Image Update," Comput. Aided Surg. 14(1-3):1-20.

Zhang et al., "Turbidity-free fluorescence spectroscopy of biological tissue", Optic Letters, Oct. 1, 2000, vol. 25, Issue 19, pp. 1451-1453.

Non Final Office Action for U.S. Appl. No. 18/893,673, mailed Dec. 12, 2025, 11 pages.

* cited by examiner

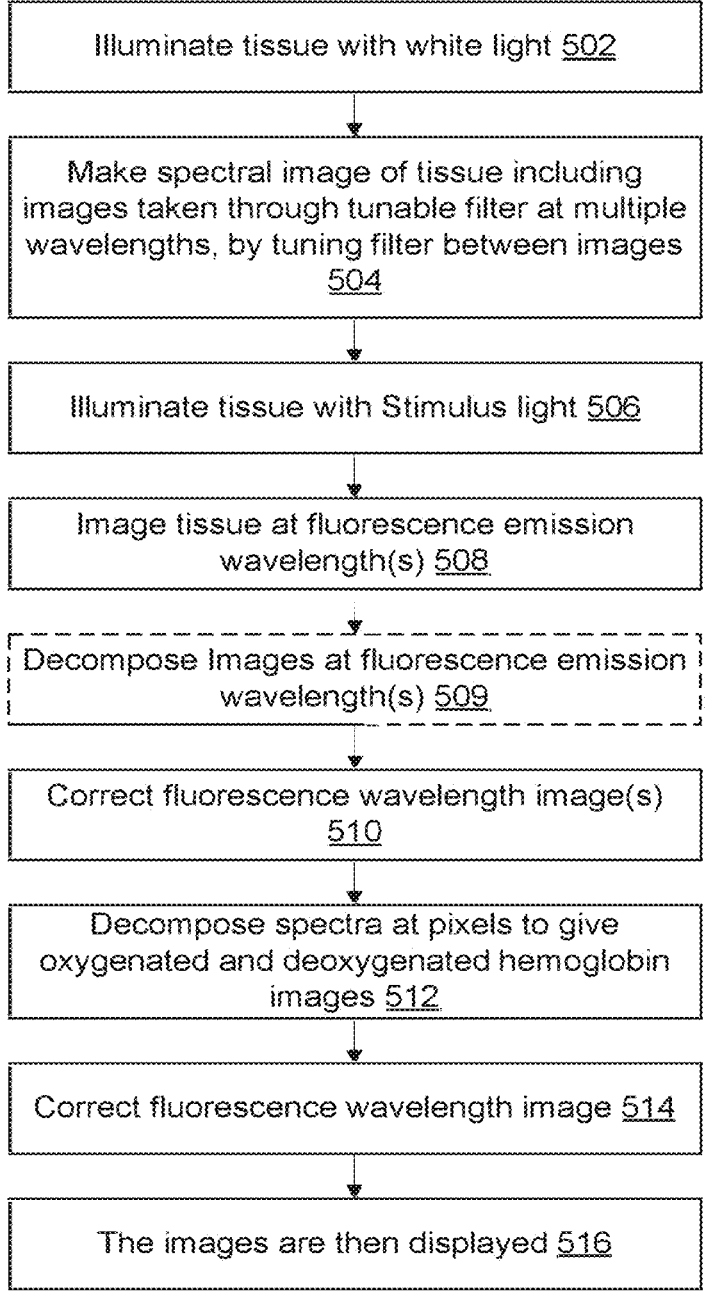

Illuminate tissue with white light 502

Make spectral image of tissue including images taken through tunable filter at multiple wavelengths, by tuning filter between images 504

Illuminate tissue with Stimulus light 506

Image tissue at fluorescence emission wavelength(s) 508

Decompose Images at fluorescence emission wavelength(s) 509

Correct fluorescence wavelength image(s) 510

Decompose spectra at pixels to give oxygenated and deoxygenated hemoglobin images 512

Correct fluorescence wavelength image 514

The images are then displayed 516

FIG. 16

METHOD AND APPARATUS FOR QUANTITATIVE HYPERSPECTRAL FLUORESCENCE AND REFLECTANCE IMAGING FOR SURGICAL GUIDANCE

RELATED APPLICATIONS

The present application is a continuation of U.S. patent application Ser. No. 18/144,767, filed May 8, 2023, which is a continuation of U.S. patent application Ser. No. 16/443,760 filed on Jun. 17, 2019, now U.S. Pat. No. 11,656,448, which is a continuation of U.S. patent application Ser. No. 14/373,443 with a § 371(c) date of Jul. 21, 2014, which is a 35 U.S.C. § 371 filing of International Application No. PCT/US2013/022266, filed Jan. 18, 2013, which claims priority to U.S. Provisional Patent Application 61/588,708 filed Jan. 20, 2012, the content of each of which is incorporated herein by reference.

GOVERNMENT RIGHTS

This invention was made with government support under grant number R01NS052274-01A2 awarded by the National Institutes of Health. The government has certain rights in the invention.

FIELD

The present application relates to the fields of surgery and imaging of surgical sites. In particular, the present application relates to hyperspectral fluorescence and reflectance imaging to improve ability of a surgeon to distinguish tissue types during surgical procedures, such as, for example, surgical procedures involving tumor resection in the brain or other organs.

BACKGROUND

There are many types of lesions treatable with surgical removal or modification. These lesions include tissues abnormal for any location in the body, such as malignant (or cancerous) tumors, and many slower-growing "benign" tumors. These lesions also include tissues that are abnormal for their location in a particular organ, but resemble normal tissues found in other locations in the body. Other lesions may incorporate material foreign to the body, including bacteria, viruses, or parasites, and associated zones of immune reactions. Still others involve developmental anomalies, such as arteriovenous malformations and berry aneurisms. Other lesions may incorporate scars and adhesions from prior illness or injury. While lesions are of many kinds, it is generally desirable for a surgeon to be able to visualize the lesion being treated and to be able to discriminate between normal and lesion tissues.

Many tumors and other lesions do not have a capsule or other connective tissue that separates them from nearby normal tissues; they may have irregular boundaries. Invasive malignant tumors in particular often have infiltrations and filaments containing malignant cells that penetrate into adjacent normal tissue. Some benign and some malignant tumors have tissue that superficially resembles tissue like that from which the tumor arose in both color and, to a certain extent, in texture. Some tumor types, including gliomas, have motile cells that may migrate a short distance away from the tumor into normal tissue; once these cells have found a hospitable location they may grow and form a new spinoff tumor. The new tumor may or may not become attached to the parent tumor, if it becomes attached it may resemble a filament of tumor. Either way, the tumor may develop a somewhat ragged edge with filaments and spots penetrating into adjacent tissue.

To reduce recurrence of many tumors after surgical treatment, including many malignancies, it is considered desirable to remove all detectable portions of the tumor.

While filaments of tumor, and motile cells, may stop extending for a time when they reach an organ capsule, resulting in tumor encapsulated in the organ, it is often undesirable to remove an entire organ or organ lobe—especially when an organ is critical for life and the tumor may not have invaded the entire organ. For example, removal of more brain tissue or spinal cord than necessary can cause life-altering neurological impairment. Similarly, it may be desirable to save as much as possible of a patient's only kidney. There are other organs and body structures where tumors may form but where it may be desirable to retain as much post-surgery organ structure and function as possible.

Invasive filaments and clones from formerly motile cell portions of tumors may not be readily visible to a surgeon—even under magnification. Other lesion types may also have portions that have color and structure that resemble nearby healthy tissue, making it difficult for the surgeon to distinguish the lesions from the healthy tissue.

A prior method of ensuring complete tumor removal while retaining as much organ as possible involves a pathologist cooperating with the surgeon. The surgeon removes the tumor and some adjacent tissue, while the pathologist immediately examines frozen sections to verify that the removed tissue includes a tumor-free margin. Should tumor portions be found to extend to boundaries of the removed tissue, extension of tumor beyond the removed tissue is assumed and more adjacent tissue is removed before closing the incision. This method tends to be slow, requiring extended anesthesia times and repeated frozen sections, and may require removal of more tissue than necessary because frozen sections can only be performed on tissue after the tissue is removed from the patient. Further, not all abnormal tissue types are readily distinguished in a frozen section. An alternative or supplemental method involves pathological examination of stained sections to verify complete tumor removal with removal of adequate margins of healthy tissue, however stained sections often take so much time to prepare that any further removal requires re-operation.

It is desirable to find improved ways of locating and identifying during surgery abnormal tissue, including tissue both abnormal for the organ and malignant tissue, including small invasive branches of tumors in tissue adjacent to tumors.

Generally, surgeons treat lesions that are visible to them during surgery. At times, lesions and tumors may lie under the surface of an organ, or under a visible and exposed surface of an operative site, where they may be obscured by overlying tissue and not readily visible, or may have poor contrast relative to surrounding stroma. It is desirable to make these lesions, including portions of malignant tumors, visible to a surgeon so that they can be more readily treated, with less normal overlying tissue damaged during treatment, than with current techniques.

It is known that some fluorescent compounds will accumulate in tumors and other abnormal tissues. Further, it is known that some prodrugs, such as 5-aminolevulinic acid (5-ALA) can be metabolized into fluorescent compounds to a greater extent in some tumor tissues than in surrounding normal stroma. Marking of tumors with 5-ALA metabolites and using resultant fluorescence at the surface of an operative site to guide surgery has been reported in the literature. For example Stummer, et al., Fluorescence-guided surgery with 5-aminolevulinic acid for resection of malignant glioma: a randomized controlled multicentre phase III trial, Lancet Oncology, Lancet Oncology, Lancet Oncol., 2006. 7(5): p. 392-401, published online Apr. 13, 2006 at oncology.thelancet.com, reports that removal of malignant glioma tumor tissue marked with fluorescent metabolites of 5-ALA and fluorescing in the visible spectrum at the surface of an operative site under violet-blue excitation light during surgical treatment of glioma improved extent of tumor resection and enhanced six month progression free survival in human subjects. Similar studies have also been performed in mice. It is expected that these results may apply for other lesion types.

Experiments have been previously conducted with tomographic fluorescent imaging of concentrations of fluorescent compounds, or fluorophores, in biological tissues. Vasilis Ntziachristos and Ralph Weissleder, Charge-coupled-device based scanner for tomography of fluorescent near-infrared probes in turbid media, Medical Physics, Vol. 29, No. 5, May 2002, have reported a use of diffuse optical tomography in "small animal geometries". The device of Ntziachristos and Weissleder, however, operates in a transmission mode. In transmission mode, light is transmitted into a turbid medium, and emitted light is detected from several points on the surface, including points on an opposite side of the turbid medium from the points where light is applied. The turbid medium of Ntziachristos and Weissleder is about one inch thick, far thinner than many human organs and tissues, because it is used in small animals such as laboratory mice. The device of Ntziachristos and Weissleder applies light to the medium from a pulsed laser, and detects light from the medium, through an arrangement of optical fibers placed about the medium. The device of Ntziachristos and Weissleder uses an intensified charge-coupled device (ICCD) camera to time-resolve the detected fluorescence in a time-domain system. Additional devices for optical imaging of biological tissues have been reported in Hillman, E., *Optical brain imaging in vivo: techniques and applications from animal to man*. Journal of Biomedical Optics, 2007. 12(5): p. 051402.

Frederic Leblond, et al, *Diffuse optical fluorescence tomography using time-resolved data acquired in transmission*, in Multimodal Biomedical Imaging II, vol. 6431. Proceedings of the International Society of Optical Imaging (2007) disclosed a time-dependent method for solving the diffusion equation (DE) for light propagation in tissues, and reconstruction algorithms for use therewith.

U.S. patent application No. 20080218727, to Djeziri, et al., entitled Method And Apparatus For Optical Image Reconstruction Using Contour Determination, 2008, describes the importance of determining tissue contours and the impact of tissue contour in diffuse optical tomography reconstruction algorithms in context of intact breast imaging. Djeziri proposes raster-scanning to determine an intensity profile, and using the intensity profile as a surface contour of the breast. He specifies using an optical fluid to fill space between the breast surface and the optical fibers of his diffuse optical tomography apparatus during diffuse optical imaging.

During surgery, use of an optical fluid to fill space between transmit and receive optical fibers is often difficult because this fluid would need to fill the surgical wound, could infiltrate into the patient, and may require a dam around the wound. Further, operation of a diffuse optical imager in transmission mode may prove difficult if the body part being operated upon is thicker than an inch—as are the brain, kidneys, and many other organs.

Most tissues of the human body are soft tissues; these tissues are inherently flexible and readily deformable. Further, many of these soft tissues interface with other tissues along boundaries where considerable movement may take place. During surgery, as adjacent structures such as skin, muscle, and bone are moved and pressure applied to soft tissues with instruments such as retractors, these tissues will deform and shift. Since these tissues may deform readily both between imaging and surgery, and during surgery, it is common for surgeons to find lesions, including tumors and foreign objects, and other surgical targets are no longer in the exact positions they occupied in preoperative images.

For a surgeon to properly treat these lesions, the surgeon must locate them during surgery. Further, for surgeons to avoid unintended damage to other nearby structures, it may also be necessary to locate particular portions of those other structures precisely during the surgery.

MRI and CT imaging are often used to provide high resolution preoperative images of surgical targets. The equipment required to make these images is bulky, expensive, and not easily incorporated into an operating-room environment. Further, the intense magnetic fields required for MRI may be incompatible with other operating room instruments and equipment, and radiation emitted by CT machines may require surgeon and staff wear bulky and heavy lead-lined garments or leave the room during intraoperative imaging.

In Hartov, et al., Error Analysis for a Free-Hand Three Dimensional Ultrasound System for Neuronavigation, Neurosurgical Focus 6 (3), 5 Aug. 1999, it was suggested that sensors, such as those produced by Ascension Technology Corporation, Milton, Vermont, be used to track a handheld ultrasound transducer in three dimensions. An alternative system uses a Stealthstation® 3-D surgical navigation system produced by Medtronic, of Minneapolis, Minnesota, for tracking instruments in three dimensions relative to a patient during surgery.

There are also chromophores naturally present in biological tissues, including human tissue. A leading such chromophore is the iron-containing heme group—as found in myoglobin and hemoglobin. Heme is generally found in both oxygenated and de-oxygenated forms in the body, and it is well known that absorption spectra of heme differs between the oxygenated and de-oxygenated forms; this difference in absorption may be used to identify tissues having different oxygen concentrations.

Many malignant tumor types have high metabolic activity due to rapid cell division and growth. These tumors often outgrow the local oxygen supply; some tumors stimulate rapid proliferation of blood vessels to overcome this, and some tumors develop core areas of low oxygen tension and may develop necrotic portions. Imaging of heme concentrations and oxygenation may assist in locating some types of malignant tumor tissue, as well as of imaging tissues such as muscle, bone marrow, liver, spleen, and blood vessels including arteriovenous malformations and aneurysms that naturally have high heme concentrations. Djeziri's diffuse optical imaging system of the breast described above is intended to visualize heme concentrations, such as those that result from rapid blood-vessel proliferation.

Muscle, including cardiac muscle, and brain activities are known to consume oxygen. A normal physiological response to this increase of oxygen consumption with activity is to dilate blood vessels to increase blood flow in affected tissue. In many diseases, including peripheral vascular disease, and cardiovascular disease, as well as cerebrovascular disease, ischemic bowel disease, the centers of some types of tumors, and other conditions, this physiological increase of flow is impaired resulting in a local decrease in oxygenation of heme. A significant decrease in oxygenation may produce pain or other signs and symptoms, as in intermittent claudication or angina. Further, mapping increases in blood flow due to brain activity can be of interest in monitoring activity in the brain.

For all these reasons, it is desirable to be able to map areas of heme concentration, to map areas of oxygenated heme and de-oxygenated heme, and to be able to view dynamic changes in oxygenation with tissue activity.

Other chromophores naturally present in some tissues, including some types of tumor tissues, are naturally fluorescent. Swartling, et al. Fluorescence spectra provide information on the depth of fluorescent lesions in tissue, Optics Letters, 2005, 44(10) pp 1934-1941 found that emissions from fluorophores have spectra that depend on the depth of the fluorophores.

The extent of resection for brain tumor procedures has been shown to correlate with patient survival and quality of life. Accurate tumor tissue identification with a surgical microscope alone can be challenging because of lack of visual or mechanical features in tissue to discriminate between normal tissue and tumor. Fluorescence-guided neurosurgery marks tumor tissue with a fluorescent contrast agent, and uses fluorescence detection technologies to identify tumor tissue using the fluorescence signals emitted from tumor tissue. Current surgical microscopes enabled for fluorescence imaging typically perform single-band, single-spectral-wavelength, detection. Although useful, significant levels of tumor tissue can be left undetected using this fluorescence imaging approach.

Prior fluorescence detection technologies in the operating room display features and functionalities such as: i) surgical microscopes modified for broad-beam fluorescence imaging currently allow for wide-field, for example, up to 50 cm$^2$, single-band, 620-720 nm, non-spectrally resolved fluorescence detection that assesses fluorescence qualitatively, without accounting for non-linear effects of tissue optical properties on the emitted fluorescence; and ii) surgical point-probe spectroscopy devices for fluorescence detection currently allow single-point, for example a 1 mm$^2$, spectrally-resolved fluorescence detection that may or may not measure fluorescence quantitatively.

SUMMARY

According to a first aspect, an imaging system is provided. The imaging system includes an illumination device for illuminating a target and a surgical microscope for receiving light from the target. The surgical microscope includes at least one optical output port at which at least a portion of the received light is provided as an output from the surgical microscope. A tunable filter receives the portion of the received light provided as the output from the surgical microscope, the tunable filter being tunable to pass a filtered portion of the received light, the filtered portion of the received light having a plurality of wavelengths selected by the tunable filter and provided as output from the tunable filter. A high-resolution, broad-bandwidth electronic camera receives the light of a plurality of wavelengths selected by the tunable filter, the electronic camera converting the light of a plurality of wavelengths selected by the tunable filter to a plurality of electrical signals. A processor processes the plurality of electrical signals to form an image of the target.

According to another aspect, a surgical microscope system is provided. The surgical microscope includes an illumination device for illuminating a target and at least one optical output port at which at least a portion of received light received from the target is provided as an output. A tunable filter receives the portion of the received light provided as the output from the optical output port, the tunable filter being tunable to pass a filtered portion of the received light, the filtered portion of the received light having a plurality of wavelengths selected by the tunable filter and provided as output from the tunable filter. A high-resolution, broad-bandwidth electronic camera receives the light of a plurality of wavelengths selected by the tunable filter, the electronic camera converting the light of a plurality of wavelengths selected by the tunable filter to a plurality of electrical signals. A processor processes the plurality of electrical signals to form an image of the target.

A real-time hyperspectral fluorescence and reflectance imaging device is provided that may, in an embodiment, be integrated into a surgical microscope. In other embodiments, the device is used with another operating room instrument or used independently. The device provides:

i) reflectance hyperspectral imaging to quantify reflectance-derived optical parameters, including but not limited to, oxygen saturation, oxy- and deoxy-hemoglobin, myoglobin, and bilirubin concentrations, and spectral distortions;

ii) reflectance hyperspectral imaging to provide information about the tissue and to provide information necessary to correct the fluorescence images for light absorption and scattering effects; and iii) quantitative hyperspectral fluorescence imaging for intraoperative guidance of neurosurgical procedures, including but not limited to brain tumor resection procedures to more accurately and quantitatively detect tumor tissue across the whole field of view using spectrally resolved fluorescence imaging.

In another embodiment, a method of imaging includes: providing a white light to a target; taking a series of images through a tunable optical filter of the target while tuning the filter to a plurality of wavelengths, the series of images forming a spectral image; providing a stimulus light to the target; taking a fluorescence emission image of the target; processing the spectral image to determine an absorption and a scattering parameter at pixels of the fluorescence emission image; and correcting the fluorescence emission image using the absorption and scattering parameters to produce a corrected fluorescence emission image.

In another embodiment, a method of imaging includes providing a white light to a target; taking a series of images through a tunable optical filter of the target while tuning the filter to a plurality of wavelengths, the series of images forming a spectral image; processing the spectral image to determine an absorption and a scattering parameter at pixels of the images; and decomposing the spectral image to provide images of components of the target, the components including specific scattering and absorbing substances expected to be in the target.

Therefore, advantages of the present system and method include the ability to provide: i) wide-field and ii) spectrally-resolved fluorescence detection for iii) quantitative fluorescence and reflectance assessments in near real time. The present system combines the advantages of current wide-field fluorescence imaging approaches, which allow for a wide field of view of the surgical field, and the spectrally-resolved and quantitative capabilities of single-point spectroscopy devices, to provide the surgeon with quantitative fluorescence and reflectance images of the whole field of view.

BRIEF DESCRIPTION OF THE DRAWINGS

The foregoing and other features and advantages of the invention will be apparent from the more particular description of preferred aspects of the invention, as illustrated in the accompanying drawings in which like reference characters refer to the same parts throughout the different views. The drawings are not necessarily to scale, emphasis instead being placed upon illustrating the principles of the invention.

(FIG. 6a, FIG. 6b, FIG. 6c) varying absorption with constant scattering; (FIG. 6d, FIG. 6e, FIG. 6f) varying scattering with constant absorption.

FIG. 16 is a flowchart of correction of a fluorescence image for absorption and scattering in a target, such as tissue.

DETAILED DESCRIPTION OF THE EMBODIMENTS

Figure 1:
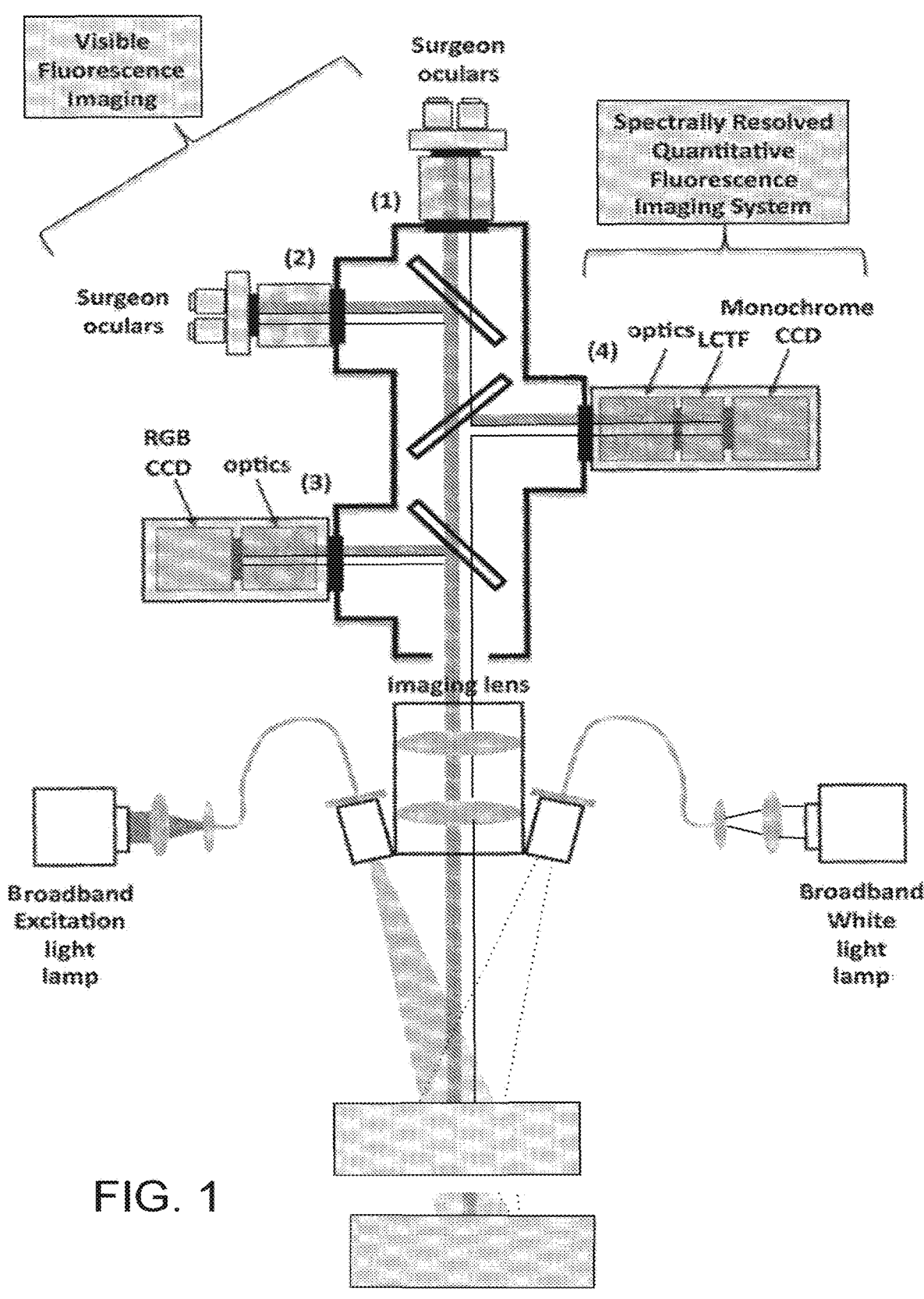
FIG. 1 contains a schematic diagram of a through-microscope spectral resolved quantitative fluorescence imaging system and a surgical microscope enabled for fluorescence imaging, according to some embodiments.

A hyperspectral imaging device is one that covers a broader range of the electromagnetic spectrum than visible light alone, such as visible and infrared light, and which is capable of resolving received light into more than the traditional three colors.

A hyperspectral imaging device is capable of acquire full field of view images of the region of interest, such as the surgical field of view, similar to broad beam fluorescence imaging devices used for wide field imaging.

A hyperspectral imaging device is one that is capable of selecting wavelengths of interest in the visible and infrared regions of the electromagnetic spectrum, and as such capable of acquiring multiple images at user-defined wavelengths of interest A hyperspectral imaging device is capable of pixel by pixel full spectra reconstruction using multiple images acquired at user-defined wavelengths of interest Qualitative, single-bandpass, visible fluorescence imaging (vis-FI) during surgery has demonstrated improved visualization of disease, bringing with it a growing interest in fluorescence imaging for surgical guidance, but not without limitations. The use of single bandpass detection in current vis-FI systems does not take full advantage of the spectral specificity of fluorophores. For example, spectrally resolved detection according to the present system enables un-mixing of non-specific autofluorescence in detected tissue to improve detection accuracy. Further, with the advent of fluorescence for intraoperative use and associated novel fluorophores for surgical guidance (for example, protoporphyrin IX (PpIX), folate receptor targeting agents, blood pooling agents like fluorescein and indocyanine green), spectrally-resolved approaches enable simultaneous un-mixing of multiple fluorescent agents from the same fluorescent signal, thus enabling in vivo imaging of multiple reporter dyes.

We have shown that quantitative assessments of tissue fluorescence, decoupled from the effects of tissue optical properties, enable us to perform accurate quantification of absolute levels of fluorescent biomarkers in brain tissue. This quantitative approach significantly improves tumor detection, thus outperforming the diagnostic capabilities of standard vis-FI, and allowing us to detect tumor tissue that would have otherwise been left undetected.

In an embodiment of an imaging system for use in surgery, quantitative hyperspectral fluorescence and reflectance imaging are provided for use during surgical procedures. The system detects cancer tissue by i) measuring a fluorescent contrast agent in a tumor and ii) measuring reflectance-derived endogenous optical markers to improve detection of diseased tissue using a quantitative hyperspectral fluorescence and reflectance imaging device that integrates with current surgical microscopes. In an alternative embodiment, quantitative hyperspectral fluorescence and reflectance imaging is provided for use independently or with another operating room instrument.

The system herein described provides near real-time quantitative hyperspectral fluorescence and reflectance imaging evaluation of tissue during surgical procedures to determine levels of fluorescent contrast agent and additional optical biomarkers in tissue in a field of view. Such information allows the surgeon to make decisions as surgery progresses and in conjunction with the surgical workflow, enabling a safer, more accurate and more effective surgical procedure through improved extent of tumor removal. A metabolic precursor to a fluorescent contrast agent—in an embodiment 5-aminolevulinic acid-induced protoporphyrin IX (PpIX) fluorescence, causes preferential accumulation of fluorophores in malignant and benign brain tumors. This system is applicable to other fluorescent contrast agents that may also mark tissue of different types, including tumor and stroma types, with high sensitivity and specificity. The present system uses a hyperspectral fluorescence and reflectance imaging device to determine fluorophore levels, such as PpIX levels, and fluorophore locations, throughout the field of view, giving the surgeon information on the levels of fluorescent agent which has accumulated in tissue and the locations of concentrations in tissue.

The additional optical biomarkers resolvable by the system, include, but are not limited to, hemoglobin concentration and oxygen saturation. These biomarkers are of use separately or in conjunction with fluorophore assessments to help inform surgical decisions.

In addition to hyperspectral imaging through the visual field of the system, the system has a probe-based hyperspectral contact point spectroscopy device, which interrogates 1 mm² of tissue at a time, and which also provides a significant improvement in tumor tissue detection. Some tumor tissue that does not display visible fluorescence using current surgical microscopes enabled for single-band fluorescence imaging, can be detected with a hyperspectral point process. The combined fluorescence and reflectance probe and method, according to embodiments described herein, measures optical biomarkers, including fluorophore concentrations, oxygen saturation, hemoglobin concentration, and scattering parameters, to improve tumor detection across a range of glioma histologies.

Fluorescence signals are strongly affected by variations in fluorophore depth, tissue absorption and transport scattering properties, i.e., tissue optical properties. A previous in vivo contact point spectroscopy technique quantifies fluorescence in tissue by compensating for the effects of tissue optical property variation and quantifies additional optical biomarkers such as hemoglobin concentration, oxygen saturation and scattering parameters. This technique was described in, for example, Valdes, P. A., *Quantitative fluorescence in intracranial tumor: implications for ALA-induced PpIX as an intraoperative biomarker*. Journal of Neurosurgery, 2011. 115: p. 11-17., which is incorporated herein in its entirety by reference.

Point spectroscopy quantitative fluorescence and reflectance results are extended to a broad-beam imaging platform in the present device.

The device sequentially acquires white light reflectance and fluorescence emissions over a broad range of wavelengths, in a particular embodiment in the range of 400-720 nm for white light reflectance and 550-720 nm for fluorescence when using, for example, PpIX. In alternative embodiments the wavelengths imaged by the hyperspectral imaging device may include additional wavelengths from 400 to 1100 nm. A light absorption-scattering correction applied across the whole imaged field of view uses reflectance data to correct the detected fluorescence spectrum. The device uses a spectrally-constrained normalization correction algorithm, in which the ratio of the reflectance near the region of the excitation wavelength and the reflectance near the region of the emission wavelength divides intensities of raw spectrally resolved fluorescence data to provide a corrected fluorescence data.

Spectral decomposition is then used to extract individual fluorophore contributions from the corrected fluorescence data, and quantify the concentration of fluorophores in tissue, and the depth of concentrations of fluorophores in tissue. In addition to the corrections required for fluorescence quantification, the reflectance data is used to retrieve additional optical parameters, including but not limited to oxygenation fraction, oxy- and deoxy-hemoglobin, myoglobin, and bilirubin concentrations, that may be of interest to a surgeon.

The devices herein described provide:
i) reflectance hyperspectral imaging to quantify reflectance-derived optical parameters, including but not limited to, oxygen saturation, oxy- and deoxy-hemoglobin, myoglobin, and bilirubin concentrations, and spectral distortions;
ii) reflectance hyperspectral imaging to determine correction parameters for correcting fluorescence images for light absorption and scattering effects; and
iii) quantitative hyperspectral fluorescence imaging. The system provides near real-time, more accurate, quantitative, and spectrally resolved fluorescence and reflectance assessments of the whole field of view. The system provides combined use of spectrally resolved reflectance and fluorescence for more accurate tissue identification across the whole field of view.

We also show phantom, pre-clinical and clinical data where we acquire high resolution spectra for every pixel in the field of view in near-real time, resolve multiple dyes and other tissue-type information intraoperatively, and provide non-subjective, absolute estimation of fluorophore concentrations in tissue, improving detection limits by one to two orders of magnitude. Overall, our technique can have broad implications for fluorescence image guidance and improving extent of resection, by enabling clinically feasible in vivo fluorophore quantification.

We have shown that quantitative assessments of tissue fluorescence, decoupled from the effects of tissue optical properties, enable us to perform accurate quantification of absolute levels of fluorescent biomarkers in brain tissue. This quantitative approach significantly improves tumor detection, thus outperforming the diagnostic capabilities of standard vis-FI, and allowing us to detect tumor tissue that would have otherwise been left undetected.

FIG. 1 is a schematic diagram of a through-microscope spectral resolved quantitative fluorescence imaging system and a surgical microscope enabled for fluorescence imaging, according to some embodiments. The surgical microscope includes two optical ports (1 and 2) associated with two respective oculars for two surgeons and a third optical port (3) that is coupled to a RGB CCD camera for video rate and still image acquisition. In some embodiments, this CCD camera is a color or black-and-white stereo camera usable for image acquisition or for surface profile extraction using stereo-optic techniques. A fourth free optical port (4) allows for integration of the portable, quantitative fluorescence and reflectance imaging device (QFI) according to the present system.

In exemplary embodiments, the QFI includes: i) an optical component that fits onto a surgical microscope, or which can be used with another operating room instrument or used independently, ii) a high-speed, tunable, wavelength-selection device, for example, a liquid crystal tunable filter, iii) a camera, and iv) a digital image processor. In an embodiment, the tunable wavelength-selection device is a liquid crystal tunable filter such as described in Nourrit, V. et al., "High-resolution hyperspectral imaging of the retina with modified fundus camera". J Fr Opthalmol 33(10), 686-692 (2010). In some alternative embodiments, the tunable wavelength-selection device is an acousto-optic tunable filter such as described in Fellers, T., et al., "Acousto-Optic Tunable Filters (AOTFs)," National High Magnetic Field Laboratory, 1800 East Paul Dirac Dr., The Florida State University, Tallahassee, FL 32310 (2004). In some alternative embodiments, the hyperspectral imaging device includes a scanning line spectrophotometer which includes an entrance slit and a rotating scanning mirror. The mirror scans the image over the slit to a dispersive element, such as a prism or a diffraction grating. A two-dimensional image sensor receives a plurality of spectra along a first dimension of the image sensor, with each spectrum being spread along the second orthogonal dimension of the two-dimensional image sensor. Such scanning line spectrophotometers are described in Gao, et al., "Snapshot Image Mapping Spectrometer (IMS) with high sampling density for hyperspectral microscopy," Opt.Express 18, 14330-14344 (2010).

The microscope has an illumination device adapted to provide illumination in both a blue or stimulus light mode for fluorescence imaging, and in a white light mode for white light reflectance imaging; wherein the stimulus light mode has a filter, or an emitter that provides specific wavelengths, such that light of fluorescence wavelength is excluded from the tissue. The QFI system connects to the free optical port of the surgical microscope.

Figure 2:
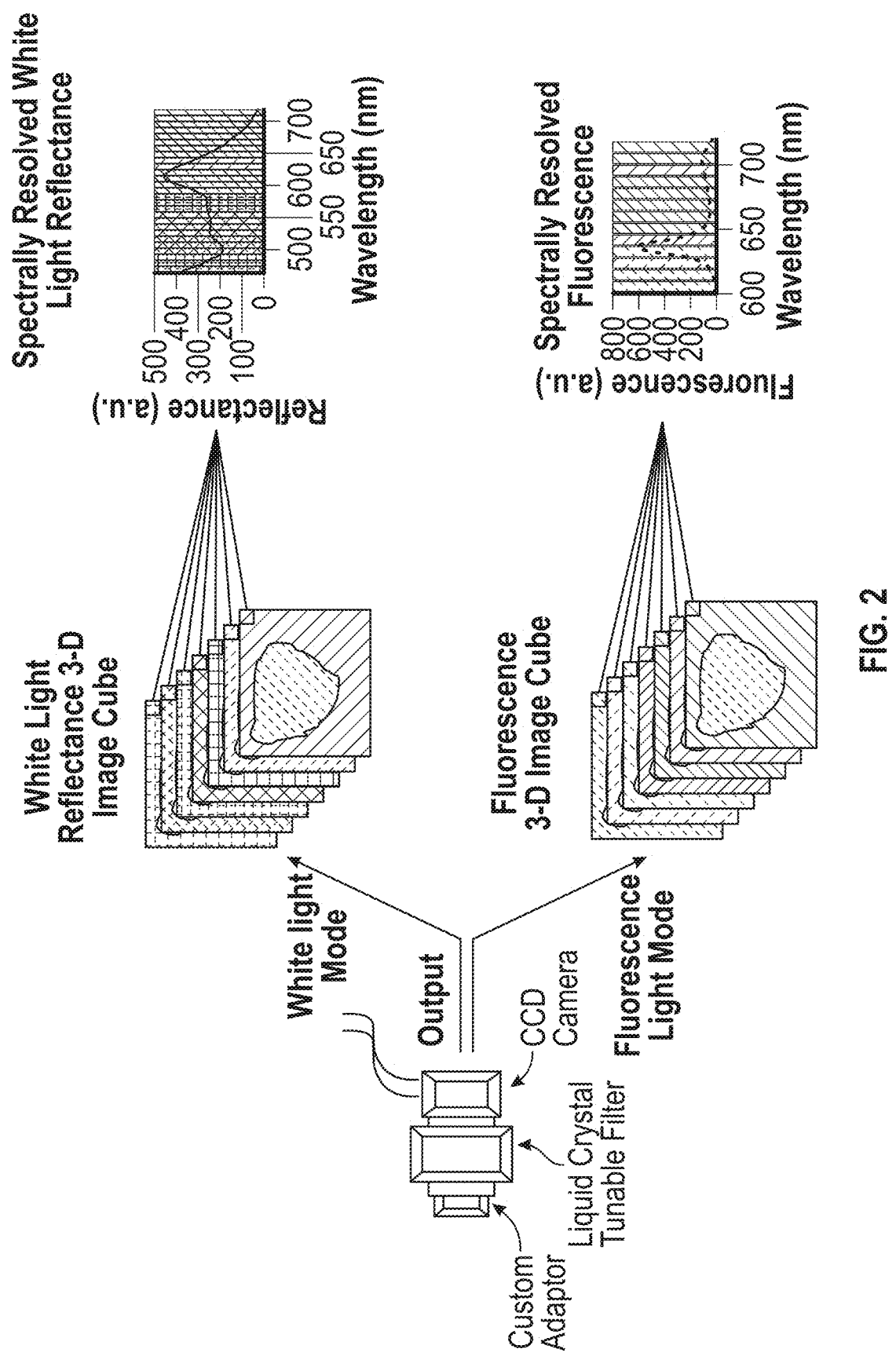
FIG. 2 contains a schematic functional block diagram of a system, according to some embodiments.

In the method illustrated in FIG. 2, a hyperspectral fluorescence and reflectance imaging device is adapted to a surgical microscope. Hyperspectral fluorescence data are acquired, processed and displayed in near real-time during a surgical procedure, enabling a surgeon to view images representing quantitative levels of fluorescent agent and additional optical markers across the whole field of view. The quantitative information aids the surgeon in making surgical decisions given the levels of optical markers present, for example, PpIX, oxygen saturation, etc.

Referring to FIG. 2, the QFI provides two sets of 3-dimensional image cubes (x,y,$\lambda$) in memory of the digital image processor, each image cube having a sequence of two dimensional images recorded by the QFI, each image of the sequence recorded at different wavelengths. The image cubes include a white light reflectance image cube under white light mode and a fluorescence image cube under a selected fluorescence excitation or stimulus light mode, such that for each (x,y) coordinate of a 2-dimensional image of the image cubes, either a reflectance or fluorescence spectrum can be reconstructed.

Figure 3:
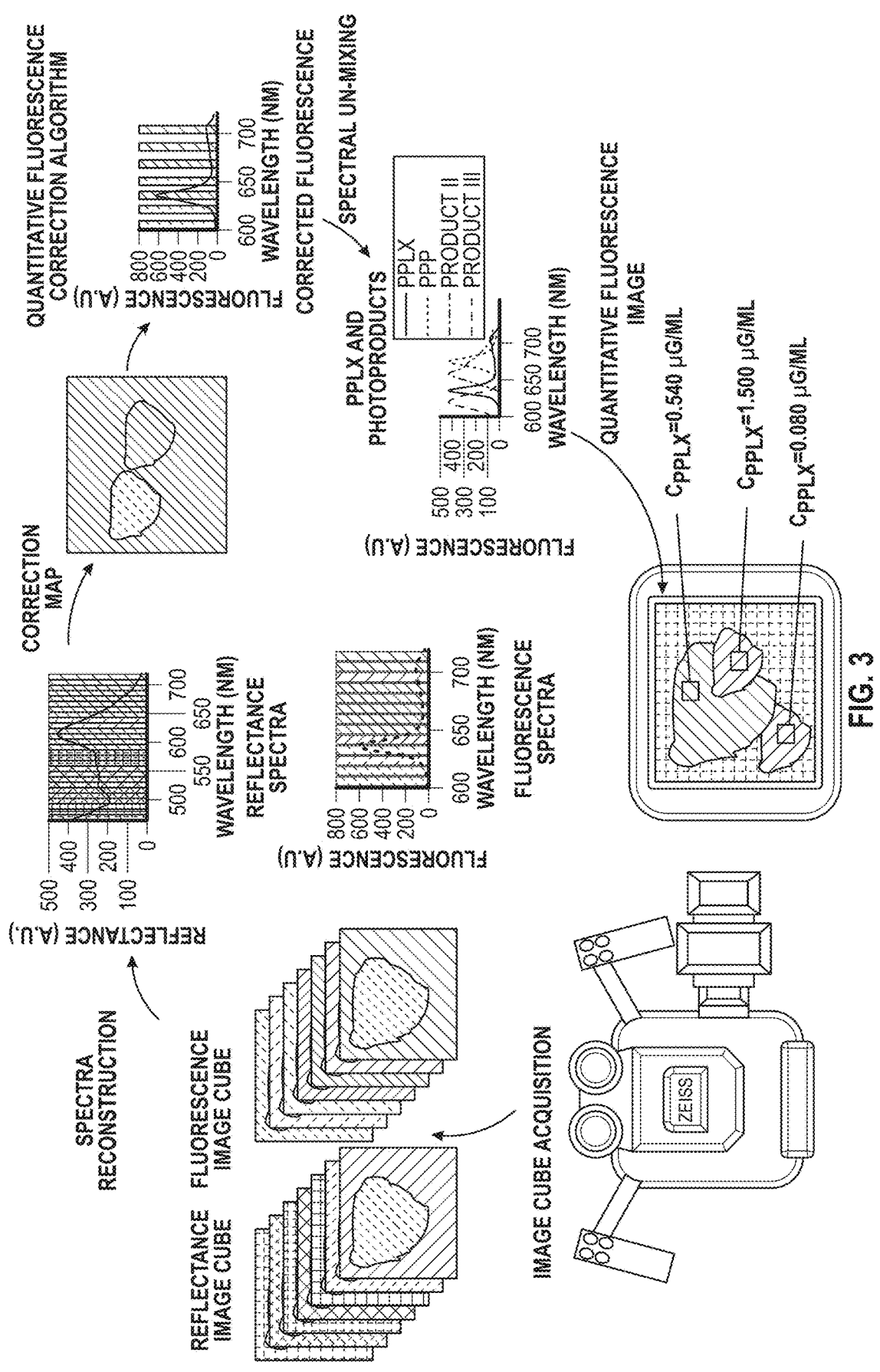
FIG. 3 contains a schematic functional block diagram of workflow of the quantitative fluorescence imaging according to some embodiments.

FIG. 3 contains a functional block diagram of workflow of the quantitative fluorescence imaging of the present device, according to some embodiments. Referring to FIG. 3, both reflectance and fluorescence image cubes are acquired for each pixel coordinate (x,y). The reflectance spectra are used in a light attenuation correction algorithm to derive a correction map which accounts for the distorting effects of tissue optical properties on the measured fluorescence at each pixel coordinate (x,y). The correction map is applied to the fluorescence spectra at each pixel coordinate (x,y) to derive fluorescence spectra which have been corrected for the effects of tissue optical properties. Spectral un-mixing techniques are applied to decouple the individual contributions of each fluorophore of interest, for example, autofluorescence, PpIX, to the corrected fluorescence spectra, and calculate a quantitative image of the absolute concentration of fluorescent biomarker in tissue, for example, $C_{PpIX}$.

The spectrally-resolved quantitative fluorescence imaging system and technique of the present system described herein were designed for seamless integration with the flow of surgery and compatibility with the state-of-the-art surgical microscopes. The imaging system is portable and affordable. In addition, the ability to spatially resolve down in the submillimeter range, enables both pre-clinical and clinical studies and case of translation between each platform.

We explored the system's capabilities to quantify a commonly used clinical fluorescent biomarker, PpIX, in tissue simulating phantoms. We noted highly accurate and sensitive PpIX biomarker quantification in near-real time compared to the raw fluorescence, $F_{RAW}$ (0.89% vs. 0.27%, $R^2$ linear regression coefficient), pointing to the ability of making fluorescence imaging in surgery quantitative and highly sensitive. Furthermore, quantitative fluorescence imaging demonstrated improved contrast compared to both vis-FI and $F_{RAW}$, with approximately 2 and 1 orders of magnitude larger dynamical range than vis-FI and $F_{RAW}$, respectively.

The imaging system provides significant improvements in intraoperative diagnostic fluorescence imaging. Further, the imaging system provides an ideal pre-clinical-to-clinical testing platform for testing of novel imaging agents and pre-clinical models, with subsequent ease of translation from bench-to-bedside. The ease of application, seamless integration into the surgical workflow, portability, reasonable costs, and small footprints, allows for implementation across modern operating rooms and visualization of multiple fluorescent biomarkers.

Results

Imaging System Design

The imaging system includes a set-up with a small footprint, which allows for ease of implementation in the operating room. The main components in a prototype embodiment include an optical adapter, a liquid crystal tunable filter (LCTF) (Cambridge Research Instruments), and a charge-coupled device (CCD) camera (Cooke Corp.) connected to a digital image processor and computer control system. The LCTF is a wavelength selection device to enable acquisition of images at each wavelength of interest and create the 3D spectrally resolved image cube. Other type of electronic camera, for example, EMCCD, ICCD, etc., or CMOS sensor cameras, which allow for collection of light and conversion to digital form, can also be used. The prototype embodiment liquid crystal tunable filter (LCTF) performs fast (50 ms) single band selection (7 nm FWHM) for filtration of incoming light in the range 400-720 nm. The LCTF displays a wavelength specific transmission response in the range $\lambda$=400-720 nm, with a max transmittance of 64% at 710 nm. The CCD camera (1396×1024 pixels; 2×2 binning; 62% quantum efficiency at 580 nm.

A fully integrated, functional system requires only standard maintenance provided to conventional surgical microscopes. The system is portable, which allows for ease of transportation between operating rooms, and installation into a commercial surgical microscope is seamless.

An optical adapter connects the main components (LCTF and camera) to an optical port of a surgical microscope, and between LCTF and a c-mount CCD camera. An LCTF performs fast (50 ms) single band selection (7 nm full width at half maximum) for filtration of incoming light in the range λ=400-720 nm. The LCTF displays a wavelength specific transmission response at a selected wavelength in the visible light range (i.e., λ=400-720 nm), with a maximum transmittance of 64% at 710 nm. The CCD camera (1396×1024 pixels; 2×2 binning; 62% quantum efficiency at 580 nm, PCO.Pixelfly, Cooke Corporation) senses the incoming light and transmits the digital counts to a computer control system. In a particular exemplary illustration, we operated in the visible region of the spectrum, given that two of the three major clinically used fluorescent imaging dyes operate in this region (i.e., fluorescein, PpIX). The system can be extended to the near infrared (650-1100 nm), given the advantages of working in this range. With the advent of novel imaging agents in the near infrared (NIR), this set up could readily accommodate either a LCTF operating in the NIR or a dual visible-NIR region LCTF.

Phantom Validation

We assessed the quantification capabilities of our QFI system. We developed a spectrally-constrained normalization algorithm that corrects the detected, raw fluorescence from the distorting effects of tissue optical properties. The varying attenuation due to tissue optical properties on both the excitation light and fluorescence emissions impact the detected fluorescence non-linearly. This varying attenuation was corrected, enabling absolute quantification of fluorophores in tissue independent of varying tissue specific attenuation. We used previously validated tissue simulating liquid phantoms of varying absorption ($\mu_a$) and reduced scattering ($\mu_s'$) at the excitation and main emission peak of PpIX (λ=405 nm and λ=635 nm, respectively) and with varying PpIX concentrations in the range 20-5000 ng/ml—the commonly found range of PpIX concentrations (lower to higher end) found in normal and pathological tissues.

Current state-of-the-art clinical systems use single band pass detection of the emitted fluorescence. We found from previous work and with our phantom studies, that vis-FI was able to visually detect concentrations no lower than ~1000 ng/ml. Here we performed an area under the curve integration of the raw optical signal in the range λ=610-720 nm, as a means to measure the raw, uncorrected fluorescence signal typically detected using contemporary clinical systems, $F_{RAW}$. We then used our quantification technique on the spectrally-resolved wide filed data to calculate the pixel-specific PpIX concentrations, $C_{PpIx}$ and thus estimate absolute PpIX levels across the full field of view. We demonstrate in our tissue simulating phantom studies that our quantitative imaging technique effectively deconvolves the non-linear distorting effects of varying optical properties on the emitted fluorescence ($R^2=0.89$, vs. $R^2=0.27$, linear regression analysis). Further, quantitative fluorescence imaging (i.e., QFI) demonstrated improved contrast compared to both vis-FI and $F_{RAW}$, with approximately 2 and 1 orders of magnitude larger dynamical range than vis-FI and $F_{RAW}$, respectively. These results demonstrate highly accurate and sensitive estimates of absolute PpIX levels in near-real time imaging mode, and that our technique improves the limit of detection of fluorescence imaging by 1-2 orders of magnitude, pushing the lower limit of PpIX found in tissues. This latter point is of importance, since it indicates that our imaging system can quantify low, yet diagnostically significant PpIX levels currently found in low-grade gliomas, the tumor histology where the impact of fluorescence imaging on patient survival could be profound.

We tested the spectral-resolving power of our imaging system on tissue simulating phantoms with homogeneously distributed and varying levels of two commonly used clinical fluorophores, PpIX and fluorescein. Our system was able to simultaneously detect and spectrally un-mix the individual fluorescence emission spectra in imaging mode across the full field of view of both fluorophores at varying concentrations. These results demonstrate the ability to do accurate simultaneous multiple-tracer imaging.

System Spatial Resolution

We first tested the spatial resolution of the system using a conventional method to measure the contrast transfer function (CTF) from a USAF 1951 standard contrast resolution target. The imaging system demonstrated submillimeter resolutions both in the vertical (214 μm and 125 μm) and horizontal directions (217 μm and 125 μm) (Rayleigh and Sparrow criteria, respectively), which are approximately 5 to 10 times smaller than the smallest length scale in which the surgeon operates. This indicates that the system demonstrates sufficient spatial resolution for both human as well as pre-clinical animal studies, which operate in the submillimeter to millimeter scales.

Spectrally-Resolved Quantitative Fluorescence Imaging Data.

Each quantitative fluorescence imaging sequence acquisition entails acquiring a 3-dimensional image cube at a 5 nm wavelength resolution (range λ=450-720 nm) acquired under white light mode for reflectance followed by a 3-dimensional image cube at a 3 nm resolution (range λ=600-720 nm) acquired under blue or excitation light mode for fluorescence.

Each 3-dimensional image cube (x, y, λ) includes a series of 2-dimensional images (x, y) (i.e., spatial dimensions) at a plurality N of specific wavelengths (λ) (i.e., spectral dimension) in the range of interest acquired under white light mode for reflectance or under blue light mode for fluorescence signals. That is, the image cube is a stack or series of 2-dimensional images taken at a plurality of wavelength settings of the tunable filter. Each individual pixel spatial coordinate (x, y) corresponds to a location on the field of view. We reconstructed high-resolution (i.e., 1 nm) full reflectance and fluorescence spectra for each pixel coordinate using a cubic spline interpolation technique for a total of 361,920 spectra per image cube (696×520=361,920).

Tissue Attenuation Correction Algorithm.

The white light reflectance spectra are used to correct the detected fluorescence spectra for the attenuation caused by tissue absorption and scattering. We used a spectrally-constrained normalization technique to estimate the intrinsic fluorescence in tissue independent of the effects of tissue optical properties by calculating the intrinsic fluorescence value, Φ, with the relationship in Eq. 1, $$\Phi^{Fluo}_{Corrected}(\lambda) = \frac{\Phi^{Fluo}_{Raw}(\lambda)}{\Phi^{Ref}_x \times \left(\Phi^{Ref}_m\right)^\alpha} \qquad \text{(Eq. 1)}$$

where $\Phi_{Raw}{}^{Fluo}(\lambda)$ is the wavelength dependent, raw fluorescence intensity; $\Phi_x{}^{Ref}$ are $\Phi_m{}^{Ref}$ the reflectance signals integrated over the ranges λ=465-485 nm and λ=625-645 nm, respectively. The range for ΦRef was determined as close to the excitation wavelength band (i.e., 405 nm) to approximate light attenuation at excitation, and the range for $\Phi_m{}^{Ref}$ was determined at the main emission peak around λ=635 nm. Our correction algorithm makes the assumption that most of the light attenuation is due to absorption at the excitation wavelength, given the high absorption due to hemoglobin, and that at the emission band, scattering dominates over absorption by 1-2 orders of magnitude more and can be corrected by an empirical power function of $\Phi_m{}^{Ref}$.

We apply our tissue attenuation correction algorithm on each pair of reflectance and fluorescence image cubes. We integrate for each pixel coordinate $(x_i, y_i)$ its corresponding high resolution reflectance spectrum to calculate $\Phi_x^{Ref}(i)$ and $\Phi_m^{Ref}(i)$. We then estimated the corrected fluorescence spectrum for each $(x_i, y_i)$ pixel coordinate, $\Phi_{Corrected}^{Fluo}(i)$, by applying the relationship in Eq. 1 to each corresponding pixel coordinate $(x_i, y_i)$ high-resolution raw fluorescence spectrum, $\Phi_{Raw}^{Fluo}(i)$. A non-negative least-squares routine is used on the corrected fluorescence spectra to spectrally un-mix the individual contributions of main fluorophores: PpIX, fluorescein, and tissue autofluorescence using the following relationship, $$c^{rel} = \left(B^T B\right)^{-1} B^T \Phi_{Corrected}^{Fluo} \qquad \text{(Eq. 2)}$$

where $B=[b_1 b_2 \ldots b_N]$ is a matrix of basis spectra for N fluorophore components (for example, PpIX, fluorescein, autofluorescence), and $c^{rel}$ is a relative concentration fluorophore vector. A system-specific calibration factor derived from the least squares regression on phantoms of known PpIX concentrations is used to convert the spectrally un-mixed relative fluorophore concentration values into absolute biomarker(s) concentrations for each pixel, $$c^{abs} = S_{cal} c^{rel} \qquad \text{(Eq. 3)}$$

where $S_{cal}$ is the system specific scalar calibration factor. We then are able to display a quantitative image map of PpIX concentrations.

Tissue Phantoms.

Liquid tissue simulating phantoms that simulate the range of optical properties found in normal brain and brain tumor using an absorber dye (McCormick) as the main absorber and Intralipid as the scattering medium were fabricated for a total of nine (9) phantoms of three (3) different optical absorption ($\mu_a^x$=20, 40, and 60 cm$^{-1}$) and scattering values ($\mu_s'^m$=8.7, 11.4, and 14.5 cm$^{-1}$) for a total of nine (9) different phantoms. For each tissue phantom, nine (9) PpIX concentrations covering the range found in brain tumors (0.019, 0.039, 0.078, 0.156, 0.313, 0.625, 1.250, 2.500, and 5.000 μg/ml) were added, and a final set with non PpIX added for a total of 90 phantoms of varying absorption, scattering and PpIX.

We acquired a pair of reflectance and fluorescence image cubes for each phantom under typical low-light operating room conditions used for fluorescence guided surgery. Each pair was processed for quantitative fluorescence imaging to estimate a PpIX concentration image map. A region of interest analysis of the corresponding $(x_i, y_i)$ pixel coordinates of the raw fluorescence image cube and on the calculated PpIX concentration image map for each phantom was used to (i) integrate the average area-under-the-curve intensity in the range 610-720 nm for the raw fluorescence spectra (i.e., $\int_{610nm}^{720nm} \Phi_{Raw}^{Fluo}(\lambda) d\lambda$)), $F_{RAW}$ and (ii) the average PpIX concentration, $C_{PpIX}$, for the quantitative image map. The former corresponds to the raw fluorescence signal of PpIX, and is equivalent to using a bandpass filter to filter out only the raw fluorescence in that range of interest.

$F_{RAW}$ and QFI derived $C_{PpIX}$ for each phantom were plotted versus the true known PpIX concentrations of each phantom. A linear regression analysis was then used to ascertain (i) the linearity of fluorescence with fluorophore concentration, which provides a measure of the non-linear effects of optical properties and the correction capabilities of our algorithm; and (ii) the limit of detection of both approaches, which provides a measure of the sensitivity of each approach to detect low levels of fluorophore.

A normalized contrast for the raw fluorescence and our quantitative approach was calculated by dividing $F_{RAW}$ Or $C_{PpIX}$ at every concentration from i=5.000-0.039 μg/ml by the $F_{RAW}$ Or $C_{PpIX}$ at the minimum concentration, 0.019 μg/ml, respectively, $$\langle nContrast_{RAW}(i) = \frac{F_{RAW}^i}{F_{RAW}^{min}} \rangle \text{ or } \langle nContrast_{QFI}(i) = \frac{QFI^i}{QFI^{min}} \rangle \qquad \text{(Eq. 4)}$$

System Spatial Resolution

A USAF 1951 (Edmund Optics) contrast resolution target was used to determine the spatial resolution of the imaging system. We imaged the USAF 1951 target under white light mode, which is made up of n=[0, 1, 2, 3] groups, each with i=[1, 2, 3, 4, 5, 6] horizontal and vertical elements consisting of black and white bar patterns. We extracted the cross-sectional intensity profiles for each element to calculate the element-specific contrast transfer function (CTF) using the following relationship, $$CTF(i) = \frac{I_{max}(i) - I_{min}(i)}{I_{max}(i) + I_{min}(i)} * 100 \qquad \text{(Eq. 5)}$$

where $I_{max}$ and $I_{min}$ are the maximum and minimum intensities of the bar pattern's cross-sectional profile. We matched the calculated element specific resolution using the following relationship $$Resolution\ (i) = \frac{1}{2^{n+\frac{i-1}{6}}} * 100\ C \qquad \text{(Eq. 6)}$$

where n is the group number, i is the element number, and resolution is given μm. We calculated the Rayleigh and Sparrow horizontal and vertical resolutions by determining the point on the graph were the CTF=26.4% or CTF=0%, respectively.

Data Processing.

Data processing and analysis was done using custom MATLAB® software (Version R2010a, The Mathworks, Inc., Natick, MA, USA)

Statistical Analysis.

Statistical analyses were performed with MATLAB. Linear regression analysis was used to determine the coefficient of determination, $R^2$. Non-parametric, Wilcoxon rank-sum (Mann-Witney) tests were used to compare differences. Two-sided P<0.05 are described as statistically significant.

Experiments provided absolute quantification of tissue concentrations of the metabolic biomarker protoporphyrin IX (PpIX) following systemic administration of the prodrug 5-aminolevulinic acid (ALA) using fiberoptic-based point fluorescence and diffuse reflectance spectroscopy in vivo. This technique significantly improves the clinical utility for detection of residual tumor during neurosurgical resection of various pathologies, including high-grade and low-grade gliomas.

In a point spectroscopy device referred to as the "Standard Probe", the full fluorescence spectrum is measured single points at the tissue surface, together with the full diffuse reflectance spectrum. A spectrally-constrained diffusion theory model is then used to determine the absorption and transport scattering spectra of the tissue ($\mu_a$ and $\mu'_s$, respectively) and these values are then used to correct the measured fluorescence spectrum yielding the true fluorescence signal. Data has been taken with the Standard Probe, this data has been used to confirm practicability of the hyperspectral imaging device described herein, and to test practicability of the spectrally-constrained normalization approach described herein. The local concentration of PpIX ($C_{PpIX}$) is then determined by spectral unmixing to eliminate contributions from PpIX photoproducts and tissue autofluorescence. A non model-based spectrally-constrained normalization approach is described herein. The potential advantages are that it simplifies the instrumentation, since only two reflectance detection channels are required. It is expected that the hyperspectral imaging device herein described will be able to provide similar information when used in vivo.

Figure 4:
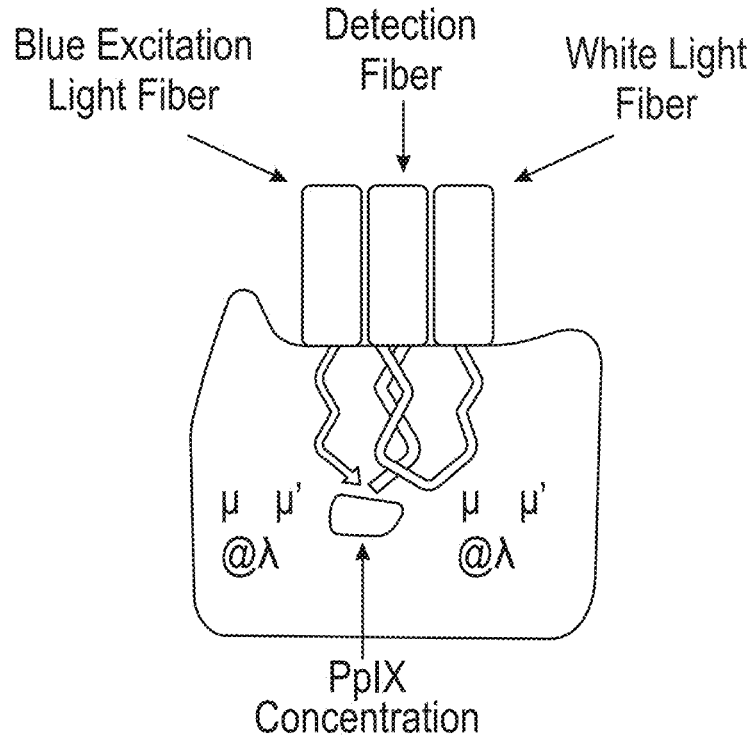
FIG. 4 is a schematic functional block diagram of the intraoperative standard probe system according to some embodiments.
Figure 5:
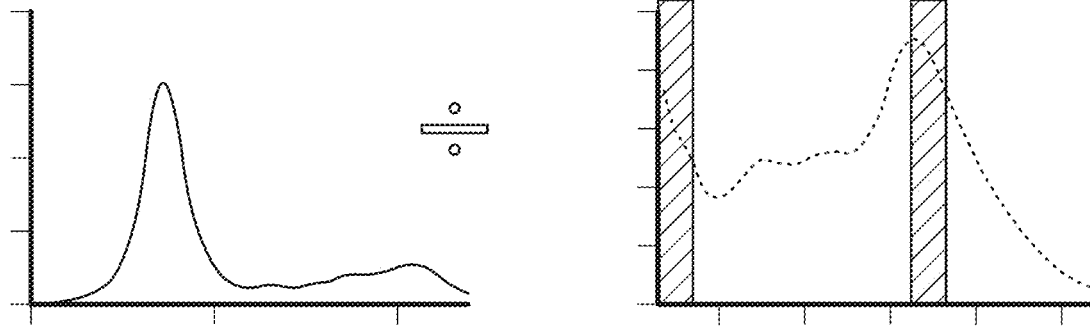
FIG. 5 illustrates the PpIX fluorescence spectrum (left) and the diffuse reflectance spectrum (right) measured in a high-grade glioma following tissue excitation with blue and white light, respectively.
Figure 6:
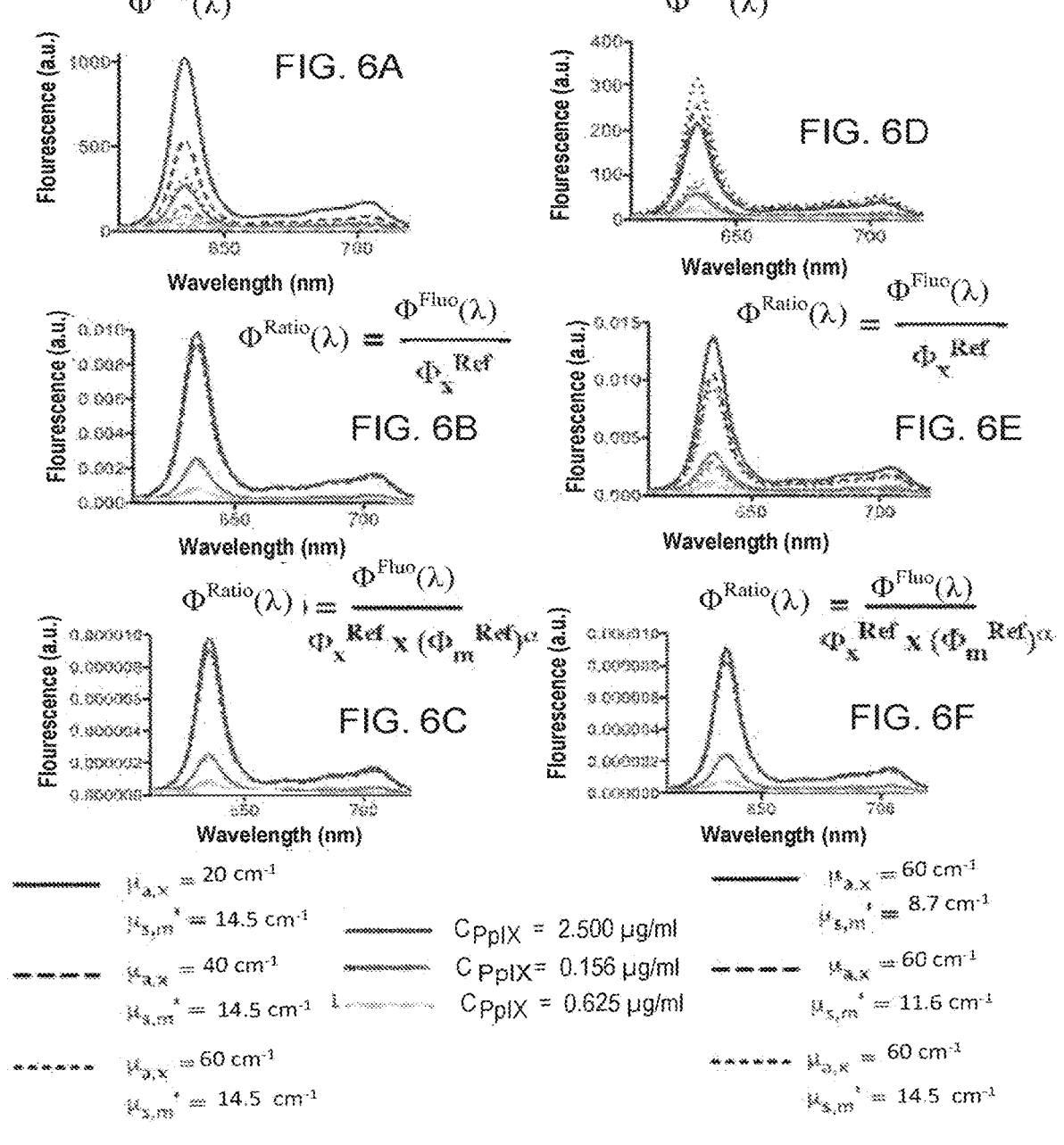
FIG. 6A-6F illustrate raw and corrected emission spectra measured for tissue phantoms, according to some embodiments. Three different PpIX concentrations and a range of absorption and scattering values were used.

FIG. 4 is a schematic functional block diagram of the intraoperative standard probe system according to some embodiments. Referring to FIG. 4, measurements are made with three adjacent optical fibers making contact with the tissue at the distal end of a 1.1 mm diameter intraoperative probe. Each fiber has a core diameter of 200 µm and the center-to-center separation between adjacent fibers is 260 µm. One fiber is coupled to a broadband light-emitting diode (LED) delivering light from $\lambda=450$ to 720 nm. Another fiber is coupled to a violet LED with center wavelength at $\lambda=405$ nm. The third fiber is coupled to a miniature fiber optic spectrometer (USB2000+, Ocean Optics Inc., FL) with light detection capabilities between $\lambda=200$ nm and 1100 nm at a spectral resolution $<\sim 1$ nm. The PpIX absorption spectrum exhibits a strong absorption band (Q-band) around $\lambda=405$ nm, so that fluorescence excitation is efficiently achieved using the violet light source fiber. The effective tissue sampling depth is $<\sim 1$ mm. White light reflectance and fluorescence emission spectra are sequentially measured using broadband and light excitation at $\lambda=405$ nm, respectively. FIG. 5 shows typical spectra acquired during a surgical resection of a high-grade glioma. That is, FIG. 5 illustrates the PpIX fluorescence spectrum (left) and the diffuse reflectance spectrum (right) measured in a high-grade glioma following tissue excitation with blue and white light, respectively. The vertical bands in the diffuse reflectance spectrum (right) indicate the detection windows used in the normalization measurements.

Spectrally-constrained normalized values, $\Phi^{Ratio}$, were computed using the formula $$Ratio() = \frac{Fluo()}{Ref_x \left( Ref_m \right)} \qquad \text{(Eq. 7)}$$

where $\Phi^{Fluo}$ is the raw measured fluorescence spectrum, and $\Phi^{Ref}_x$ and $\Phi^{Ref}_m$ are the spectrally-integrated reflectance signals in the range $\lambda=465$-485 nm and $\lambda=625$-645 nm, respectively. The wavelength range for $\Phi^{Ref}_x$ was chosen to be as close as possible to the fluorescence excitation band in order to correct for tissue attenuation of the excitation light. The second band samples the main PpIX fluorescence emission peak around $\lambda=635$ nm. The underlying assumptions of Eq. (7) are: (1) that most of the spectral distortion effect is due to tissue absorption at the excitation wavelength, and (2) that the impact of light diffusion in the emission band, where scattering dominates over absorption, can be corrected by further dividing the raw fluorescence using an empirical power function of $\Phi^{Ref}_m$.

Three separate sets of measurements with PpIX were conducted to evaluate the accuracy of the spectrally-constrained normalization algorithm: (1) in tissue-simulating phantom experiments with a range of optical properties consistent with human brain tissue, (2) using ex vivo animal brain tumor tissue, and (3) using in vivo clinical data previously acquired with the Standard Probe during resection procedures in brain tumor patients. For each measurement, a background spectrum was acquired and subtracted from the raw fluorescence in order to account for the dark noise of the instrument, and the resulting spectrum was corrected using Eq. (7) for values of the empirical parameter a ranging from −2 to 2. The corrected spectra were then unmixed to separate the contributions of the main fluorophores, namely PpIX, its photoproducts and tissue autofluorescence. The resulting pure PpIX spectra were then normalized to a calibration factor, which in turn was derived from the slope of the linear regression fits in phantoms with known dye concentrations, in order to extract an absolute PpIX concentration, $C_{PpIX}$.

Figures 7, 8, 9, 10:
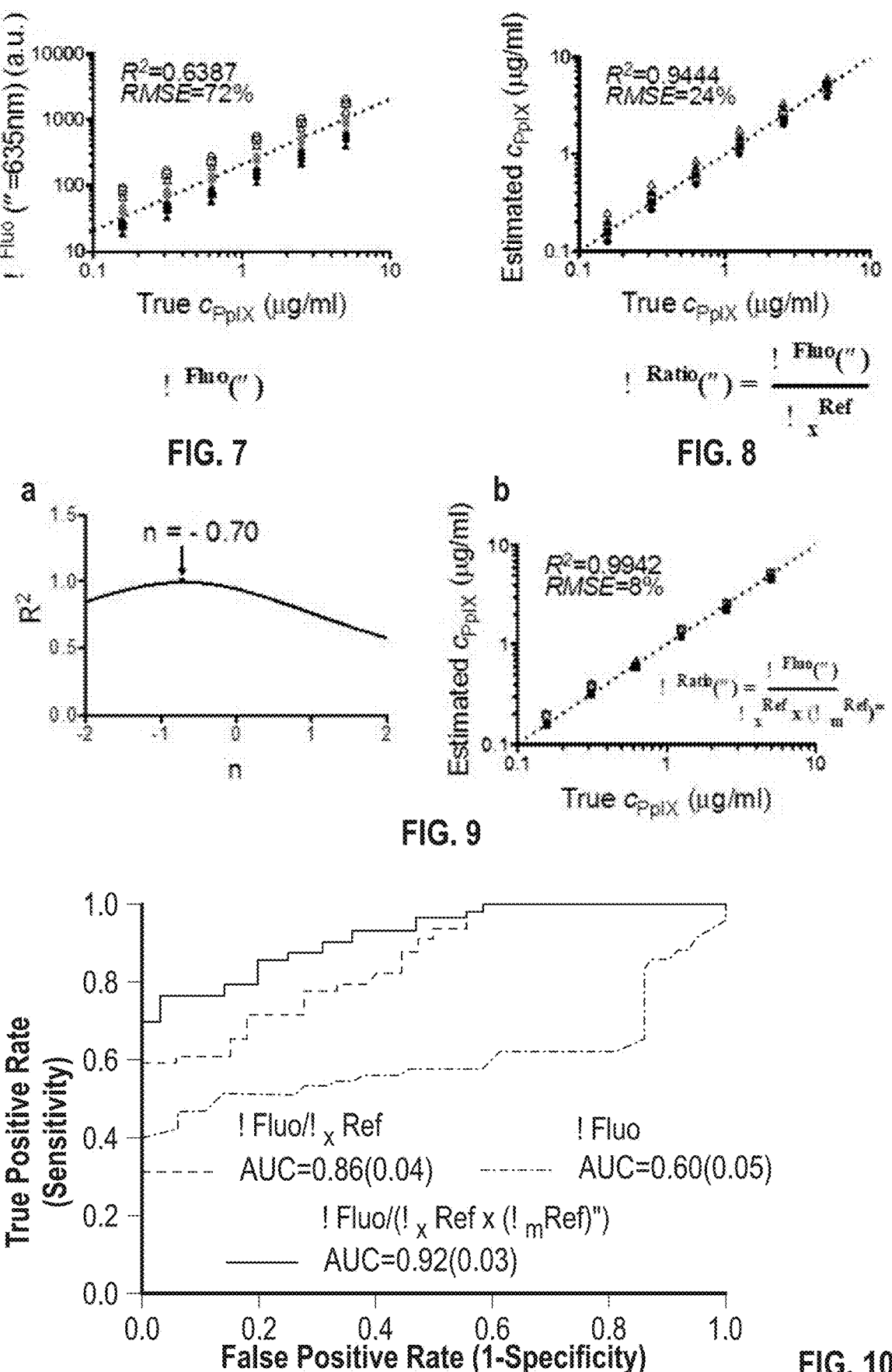
FIG. 7 illustrates quantification of PpIX concentration in phantoms based on raw fluorescence intensity (X=635 nm), according to some embodiments.
FIG. 8 illustrates quantification of PpIX concentration in phantoms based on (a) raw fluorescence intensity ($\lambda$=635 nm), and (b) estimated $C_{PpIX}$ levels derived following correction of the raw fluorescence, according to some embodiments.
FIG. 9 illustrates (a) empirical determination of the optimal $\alpha$ value for PpIX quantification and (b) relationship between the estimated an actual PPIX concentration in phantoms following correction of the raw fluorescence, according to some embodiments.
FIG. 10 contains ROC curves quantifying the performance of three different fluorescence measurement schemes for optical datasets acquired in vivo during 14 brain tumor resection procedures.

The phantoms comprised Intralipid (Fresenius Kabi, Uppsala, Sweden) which provided the tissue-like background scattering, yellow food coloring (McCormick, London, Ontario) as the absorber and PpIX. Nine phantoms of differing optical properties were prepared, and a total of six concentrations of PpIX (0.15625, 0.3125, 0.625, 1.25, 2.5, and 5 µg/ml) for each phantom were mixed, giving a total of 54 separate phantoms with different absorption coefficient (µa), reduced scattering coefficient (µs') and fluorophore concentration. In order to mimic human brain tissue, the absorption and reduced scattering at the excitation wavelength ranged from µa=20 to 60 cm-1 and µs'=15 to 25 cm-1, respectively, and at the emission wavelength ranged from µa=0.02 to 0.06 cm-1 and µs'=8.7 to 14.5 cm-1. Fluorescence and reflectance measurements were made for each phantom using the Standard Probe. FIG. 6A-6F illustrate raw and corrected emission spectra measured for tissue phantoms, according to some embodiments. Three different PpIX concentrations and a range of absorption and scattering values were used: (FIG. 6a, FIG. 6b, FIG. 6c) varying absorption with constant scattering; (FIG. 6d, FIG. 6e, FIG. 6f) varying scattering with constant absorption. The value of $\alpha=-0.7$ is used in FIG. 6c and FIG. 6f. Illustrated is the marked effects of varying absorption (FIG. 6(*a*) and scattering (FIG. 6(*b*)), on the measured fluorescence spectra, primarily in the intensity, with some distortion also of the spectral shape. In tissue, the latter is greatly due to the strong spectral dependence of hemoglobin absorption. Dividing the measured spectrum by $\Phi$Refx (FIG. 7b) partially corrects for changes in absorption and, to a lesser extent, for changes in scattering (FIG. 7e). Normalization to a function of $\Phi$Refx and $\Phi$Refm as in Eq. (7) can further correct for changes in both absorption (FIG. 7c) as well as scattering (FIG. 7f), and yield quantitative fluorescence spectra that are largely independent of variations in the optical properties. As shown below, the optimal tissue-specific empirical parameter a is determined experimentally using the tissue-simulating phantoms (or, for example, Monte Carlo modeling) in order to achieve the highest accuracy in CPpIX. As in previous studies, the spectral unmixing algorithm was applied to the corrected fluorescence spectrum, using the known PpIX emission spectrum as input. A calibration factor, derived from the linear regression fit of $\Phi$Ratio(□) against the true concentration was then applied to the pure PpIX spectrum to determine CPpIX. FIG. 7 and FIG. 8 illustrates quantification of PpIX concentration in phantoms based on FIG. 7 raw fluorescence intensity ($\lambda$=635 nm), and FIG. 8 estimated CPpIX levels derived following correction of the raw fluorescence, according to some embodiments. FIG. 7 and FIG. 8 shows, as a function of the true PpIX concentration, both the raw fluorescence intensity and the calculated CPpIX following correction only for the strong absorption effects at the excitation wavelength. There is a significant improvement in the goodness-of-fit, from R2=0.639 (RMSE=72%) for the detected fluorescence ($\Phi$Fluo) to R2=0.944 (RMSE 24%) using a correction by the reflectance close to the excitation only ($\Phi$Fluo/$\Phi$Refx). Correction by the product of $\Phi$Refx$\Phi$Refm$\square$ provided the greatest improvement, with R2=0.984 (RMSE 13%), using a=–0.7 (FIG. 9(*a*)). This algorithm is applied in the subsequent ex vivo tissue and clinical studies. FIG. 9 illustrates (a) empirical determination of the optimal $\alpha$ value for PpIX quantification and (b) relationship between the estimated an actual PPIX concentration in phantoms following correction of the raw fluorescence, as described herein.

The spectrally constrained normalization method was then evaluated in terms of its efficacy to quantify $C_{PpIX}$ in biological tissue. $1\times10^6$ cells from the human glioma VX2 line were orthotopically implanted to a depth of 2 mm in the brains of five mice. Following three weeks of incubation, 100 mg/kg body weight of ALA (Sigma-Aldrich Inc., MO) was injected via the tail vein, and the animals were subsequently sacrificed by cervical dislocation under anesthesia at 0.5, 1, 2, 3 and 4 h later, respectively. The brains were then removed intact and measurements made with the Standard Probe at three different locations for each sample. The probe measurements (fluorescence and reflectance) were used to compute the ratio in Eq. (7) for $\alpha$=–0.7, from which the $C_{PpIX}$ value was calculated, as above. For comparison, quantitative fluorimetric measurements of $C_{PpIX}$ were made on ex vivo brain tissue samples using an established technique. Statistical analysis (paired Student's t-test) showed no significant difference between the fluorimetric measurements and ratiometric estimates (p=0.33). These results represent an initial demonstration that absolute quantification of PpIX in tissue using the ratiometric approach according to some embodiments is feasible and accurate.

The Standard Probe has been used in ALA-induced PpIX fluorescence guided resection of human brain tumors. Here, we revisit the same clinical data and retrospectively apply the ratiometric algorithm in patients with a diagnosis either of glioma (N=5), meningioma (N=6) or metastatic brain tumors (N=3). Receiver operating characteristic (ROC) curves were generated to assess the performance of the normalization approach for detecting abnormal tumor tissue. FIG. 10 contains ROC curves quantifying the performance of three different fluorescence measurement schemes for optical datasets acquired in vivo during 14 brain tumor resection procedures. FIG. 10 shows the ROC plots of the quantified $C_{PpIx}$ using two ratiometric approaches compared with the raw measured fluorescence ($\Phi^{Fluo}$) intensity peak at $\lambda$=635 nm for each tumor type. There was a highly statistically significant difference in the performance of the normalization approach, with the area under the curve (AUC) increasing to 0.92 (STD=0.03) from the value of 0.60 (STD=0.05) for the raw fluorescence signal.

The use of ALA-induced PpIX fluorescence guidance during tumor resection is gaining importance in the neurosurgical community, and there is increasing evidence that quantitative techniques that augment the visual fluorescence assessment of the surgeon yields clinical benefit. Our previous work demonstrated this using a full-spectrum device and algorithm for quantitative point measurements. According to some embodiments, an optimized non model-based spectrally-constrained normalization approach is used for PpIX quantification, applying a semi-empirical algorithm to correct for the distorting effects of optical attenuation in tissue. The advantage is that this is technically simpler in point-mode but is also translatable into wide-field quantitative fluorescence imaging mode more easily than the full-spectrum approach. A possible limitation compared to the Standard Probe method, which is, at least in principle, universal and does not require tissue-dependent calibration, is that it requires experimental determination of the empirical optimization parameter, a, as well as a calibration factor derived from the linear regression fit using phantoms of known concentrations. Further detailed studies are required to establish any other limitations to the accuracy for absolute fluorophore quantification in vivo and this work is in progress, as is initial testing in wide-field quantitative imaging mode.

These approaches to determining $C_{PpIX}$ in vivo (or the concentration of other exogenous molecules) may also be of value in applications such as photodynamic therapy in order to monitor and optimize the dose of photosensitizer and the drug-light time interval for treatment.

Figures 11, 12:
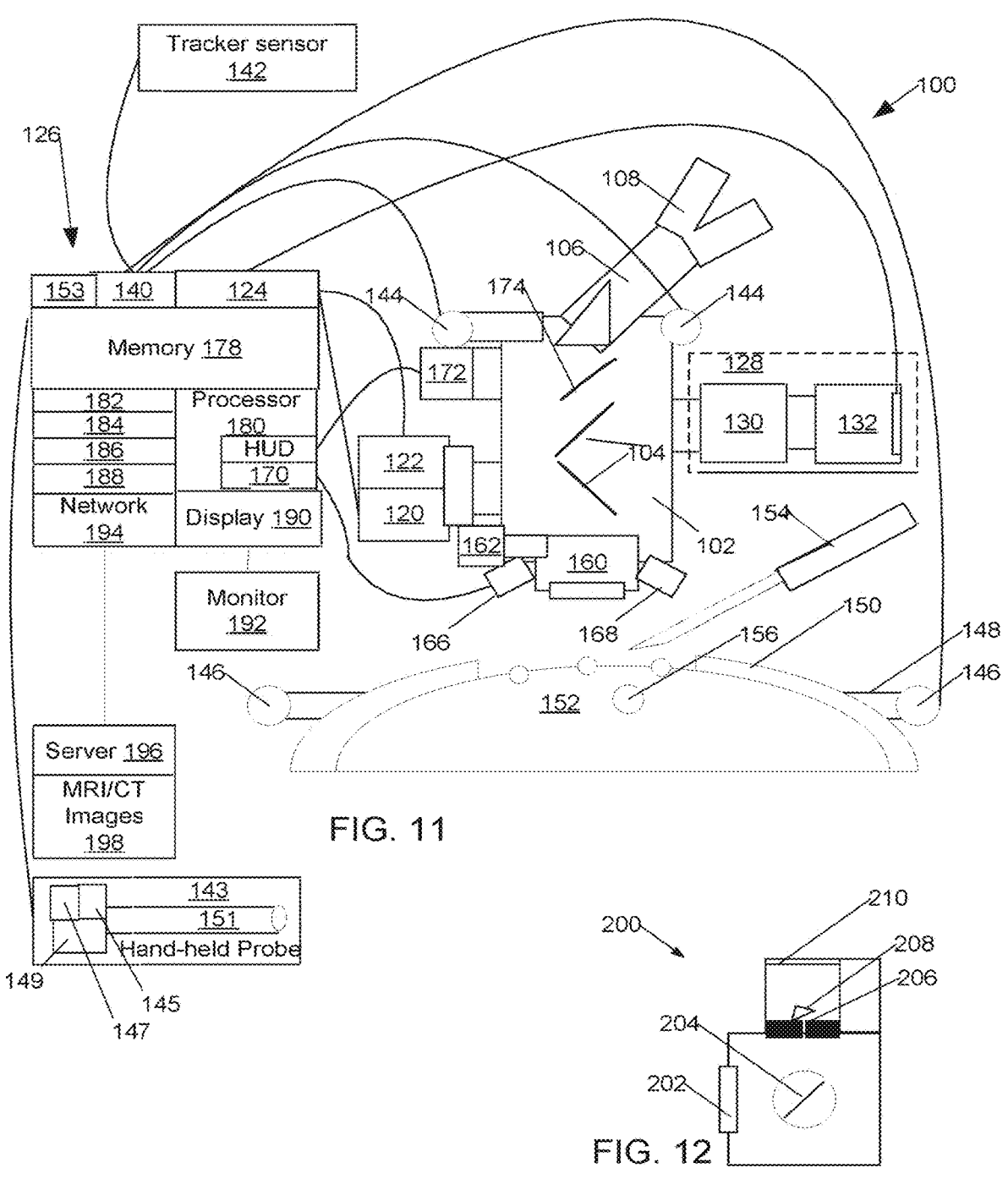
FIG. 11 contains a schematic block diagram illustrating a system for supporting surgery, according to some embodiments.
FIG. 12 is a schematic block diagram of a hyperspectral imaging device, according to an alternative embodiment.

FIG. 11 is a schematic block diagram illustrating a system 100 for supporting surgery, according to some embodiments. The system of FIG. 11 includes a microscope body 102, which has multiple beam splitters 104 that permit light to be diverted to several optical ports simultaneously. Attached to a first optical port of body 102 is a tube 106 leading to a surgeon's binocular optical eyepieces 108.

Attached to a second optical port of body 102 are a first high definition electronic camera 120 and a second high definition electronic camera 122. Cameras 120, 122 are coupled to provide images to image capture interface 124 of a digital image processing system 126. Attached to a third optical port of body 102 is a hyperspectral imaging device 128 that in an embodiment has a tunable filter 130 adapted to receive light from body 102 and a high resolution broad-bandwidth electronic camera 132. The camera 132 of the hyperspectral imaging device 128 is also coupled to provide images to image capture interface 124 of the digital processing system 126. In an embodiment, tunable filter 130 is a liquid crystal tunable filter. In an alternative embodiment, tunable filter 130 is an acousto-optic tunable filter.

FIG. 12 is a schematic block diagram of a hyperspectral imaging device, according to an alternative embodiment. In an alternative embodiment, hyperspectral imaging device 128 of FIG. 11 is replaced with the hyperspectral imaging device of FIG. 12. In the hyperspectral imaging device of FIG. 12, light received through optical interface port 202 is scanned by a rotating mirror 204 across a spectrometer slit 206. Light passing through spectrometer slit 206 is dispersed according to wavelength by a dispersive device 208, such as a prism or a diffraction grating, and thence onto a planar image sensor 210 such that each column of planar image sensor 210 provides a spectrum of light received at a corresponding point in slit 206, and light received at slit 206 corresponds to light scanned from a row of a virtual image received through microscope body 102.

Referring again to FIG. 11, a tracker interface 140 of the image processing system 126 is coupled to use sensors 142 rigidly attached to a reference location within an operating room to track locations of microscope location sensors 144 and patient location sensors 146. Microscope location sensors 144 are rigidly attached to the microscope body 102, and patient location sensors 146 are attached to a frame 148 that may be attached to a patient while the patient is undergoing a surgical procedure. In a particular embodiment, frame 148 is adapted to be attached to a patient's skull 150 by screws (not shown) for the duration of a neurosurgical procedure during which the patient's brain 152 is exposed, and during which patient's brain 152 may be operated on with surgical instruments 154 to remove one or more lesions 156.

Microscope body 102 also has zoom optics 160, adapted for operation by a zoom motor/sensor 162, and a focus adjustment (not shown) adapted for operation by a focus motor (not shown). The microscope also has multiple illuminators 166, 168. In an embodiment, illuminators 166, 168 include white-light illuminators 166, and fluorescent stimulus illuminators 168, operating under control of an illumination interface 170 of the image processing system 126. The microscope body also has a heads-up display (HUD) projector 172 capable of providing graphical images through a combiner 174 of body 102 such that the graphical images are presented for viewing by a surgeon through surgeon's eyepieces 108. The surgeon's field of view through the operating microscope and its associated HUD is co-registered with that of the imaging system, allowing display of tissue classifications and hyperspectral imaging results superimposed on visible brain tissue, one-to-one comparisons, and intraoperative surgical decision making. At standard working distances between microscope and surgical cavity, surgical tools 154 fit between objective 160 and tissue 152.

Image processing system 126 also has a memory 178 into which image capture interface 124 saves images received from cameras 120, 122, 132; and at least one processor 180. Processor 180 is adapted for executing processing routines such as surface profile extraction routines 182, brain deformation modeling routines 184, fluorescence depth modeling routines 186, and hyperspectral image processing routines 188 stored in memory 178 and operable on images stored in memory 178. Processor 180 is also adapted for preparing images for display through display interface 190 onto monitor 192, and for communicating through network interface 194 to server 196; server 196 has a database containing information derived from preoperative MRI and CAT scans 198.

Among the image processing routines in memory of image processing subsystem 126 also has a classifier for classifying tissue types according to a combination of fluorescence and backscatter information. In a particular embodiment, the classifier is a K-nearest-neighbor classifier.

Image processing system 126 is also interfaced to a handheld backscatter fluorescence probe 143 that acts as a single-channel, single-point subset of the fluorescence imaging microscope. Probe 143 has white 145 and fluorescence stimulus 147 illuminators, and a spectrophometric detector 149, the illuminators 143, 145, and detector 149 coupled through an optical fiber and lens subsystem 151 to apply light to, and read light from, a single point on tissue surface. The probe couples into the image processing subsystem 126 through a probe interface 153.

Operation of the system 100 has several modes, and each mode may require execution of several phases of processing on processor 180, executing one or more of several routines, as mentioned above. For example, processor 180 can execute the hyperspectral image processing routine to perform the hyperspectral fluorescence and reflectance imaging of the system, as described above in detail. The hyperspectral fluorescence and reflectance imaging can also be performed in connection with stereo-optical extraction, using images captured by stereo cameras 120, 122, to perform tissue surface extraction and modeling, as described in U.S. Provisional Patent Application No. 61/583,092, filed in the United States Patent and Trademark Office on Jan. 4, 2012, and incorporated herein in its entirety by reference. The tracking using tracking sensor 142, patient location sensors 146 and microscope location sensors 144 described above can be used in performing the brain deformation modeling routine. The hyperspectral fluorescence and reflectance imaging can also be performed in connection with fluorescence depth modeling, as described in U.S. patent application Ser. No. 13/145,505, filed in the United States Patent and Trademark Office on Jul. 2, 2011, and incorporated herein in its entirety by reference, and described below in detail, where fluorescence and reflectance spectral information is derived from hyperspectral imaging device 128. It should be noted that in the referenced U.S. patent application Ser. No. 13/145,505 and described below in detail, the depth modeling is described as using a ratio of images at two wavelengths. Depth modeling using the hyperspectral fluorescence imaging of the present system can be improved with a modified process in which several ratios are used simultaneously using a fitting routine.

A phase-3 human trial of surface fluorescent microscopy during surgical removal of malignant tumors marked with 5-ALA showed increased survival following surgery when all fluorescent tumor visible at excision cavity surfaces are removed; see Stummer, et al., Fluorescence-guided surgery with 5-aminolevulinic acid for resection of malignant glioma: a randomized controlled multicentre phase III trial, Lancet Oncol., 2006. 7 (5): p. 392-401, published online at oncology.thelancet.com.

5-ALA may also be usable to locate tumors in other organs. In particular, 5-ALA has been shown to be preferentially metabolized into protoporphyrin IX in tumors of the prostate as compared to protoporphyrin IX production in surrounding normal prostate tissue. This may offer the opportunity to remove the prostate tumors with reduced risk of damaging nerves responsible for penile sensation and erection; thereby preserving functions thought important by many patients.

In yet another embodiment, dye administered to a patient to locate a tumor contains a fluorescent molecule or prodrug metabolized into fluorescent molecules in-vivo that is attached to a monoclonal antibody having specificity for tumor tissue.

In an embodiment tailored for use with tumors metastatic from a distant organ (not shown) such as lung, dye administered to a patient comprises a fluorescent molecule or prodrug attached to an antibody, such as a monoclonal antibody, having specificity towards a tissue type of the distant organ. Because many metastatic tumors retain some cell-surface markers similar to those of the parent tissue, dye preferentially delivers the fluorescent molecule or prodrug to the tumor tissue, while delivering a substantially lower concentration of the fluorescent molecule or prodrug to the organ.

A surgeon visualizes the tumor through the hyperspectral imaging device described herein.

Typically, tumors and organs are light propagation media where absorption and scattering is particularly important at short wavelengths, making them seem opaque to visible light. Consequently, the white light images give good resolution but do not give good visibility of features beneath a surface of the tissue of tumor and organ. In particular, light at the blue end of the visible spectrum is often absorbed and scattered within less than a millimeter of the surface, rendering it difficult to see deeper structures. Further, because fine invasions of tumor may have color and structure superficially resembling that of surrounding tissues, these fine invasions of tumor at the surface may not be readily visible to the surgeon. However, the interaction of far-red and near-infrared light with biological tissue is such that propagation is inherently different when compared to that of visible light. For far-red and near-infrared light, scattering is still important but absorption by the main contributing chromophores such as hemoglobin and water are dramatically reduced (see FIG. 23). This provides an opportunity for imaging structures embedded deeper into the tissue using far-red and near-infrared light.

In an alternative embodiment, the monochromatic illuminator provides red or near infrared light between 600 and 1000 nanometers wavelengths, this light is capable of deeper penetration into organ and tumor than blue or green light and is within the range of wavelengths that can be detected by available electronic cameras. The wavelength used is chosen to be appropriate for the fluorophore used to label the organ or tumor.

The hyperspectral imaging device herein described may, in an embodiment, be operated to provide basic fluorescent imaging. This is done by illuminating the tissue with a light at a stimulus wavelength, in a particular embodiment by illuminating with a blue light-emitting diode (LED) having a filter to exclude illumination at a fluorescence emission wavelength. The tunable liquid-crystal filter is then set to pass only light at the fluorescence emission wavelength. This provides the surgeon with non depth-resolved information pertaining to fluorophore distribution beneath the surface; this information may be somewhat hazy due to scattering in the tissue.

In an embodiment, multiple monochromatic illuminators are provided, and the tunable liquid crystal filter adjusted appropriately, permitting rapid selection of surface and deep imaging wavelengths, and wavelengths suitable for different fluorophores.

The surgeon views the fluorescence image information on monitor 192 before, after, or at intervals while using surgical instruments such as surgical tools 154 to remove or destroy part or all of tumor 156.

When the surgeon wants to determine if any tumor tissue remains in the organ 152, the surgeon triggers the system to obtain new fluorescence tomographic image information, views that information of monitor 192, and may remove additional portions of tumor 156 and organ 152.

In an embodiment, blue or ultraviolet monochromatic stimulus-wavelength emitters have peak emission between three hundred fifty and four hundred five nanometers to induce visible fluorescence from protoporphyrin IX in tumor. Alternative embodiments may replace blue or ultraviolet flood emitters with, or provide an additional set of monochromatic flood emitters, for providing stimulus specifically appropriate to a fluorophore other than protoporphyrin IX present in tumor. For example, near-infrared monochromatic emitters may be used with other dyes such as those based on indocyanine green. In an embodiment, monochromatic emitters are LEDs; LEDs are available in a wide variety of spectral characteristics, can provide intense light, and are small and easy to use. In an alternative embodiment, monochromatic emitters are a tungsten halogen or high intensity discharge light source equipped with a monochromatic filter for transmitting a wavelength appropriate for inducing fluorescence in fluorophores of, or metabolically produced from, the dye in use. Such an alternative light source may also include optical fibers and lenses for directing light from the monochromatic filter to the tissue and tumor.

In some applications of the microscope other than open brain surgery, there may also be a matching liquid applied to the subject to give the area being interrogated a geometry that is simpler to model.

In an embodiment, a left and right stereo image pair is captured 402. This image pair is used by the processor 180 to extract a surface profile of the tissue. Image cubes are then captured with the hyperspectral imaging device and placed in memory as previously described. A computer model of diffuse scattering in the tissue is then constructed.

Figure 14:
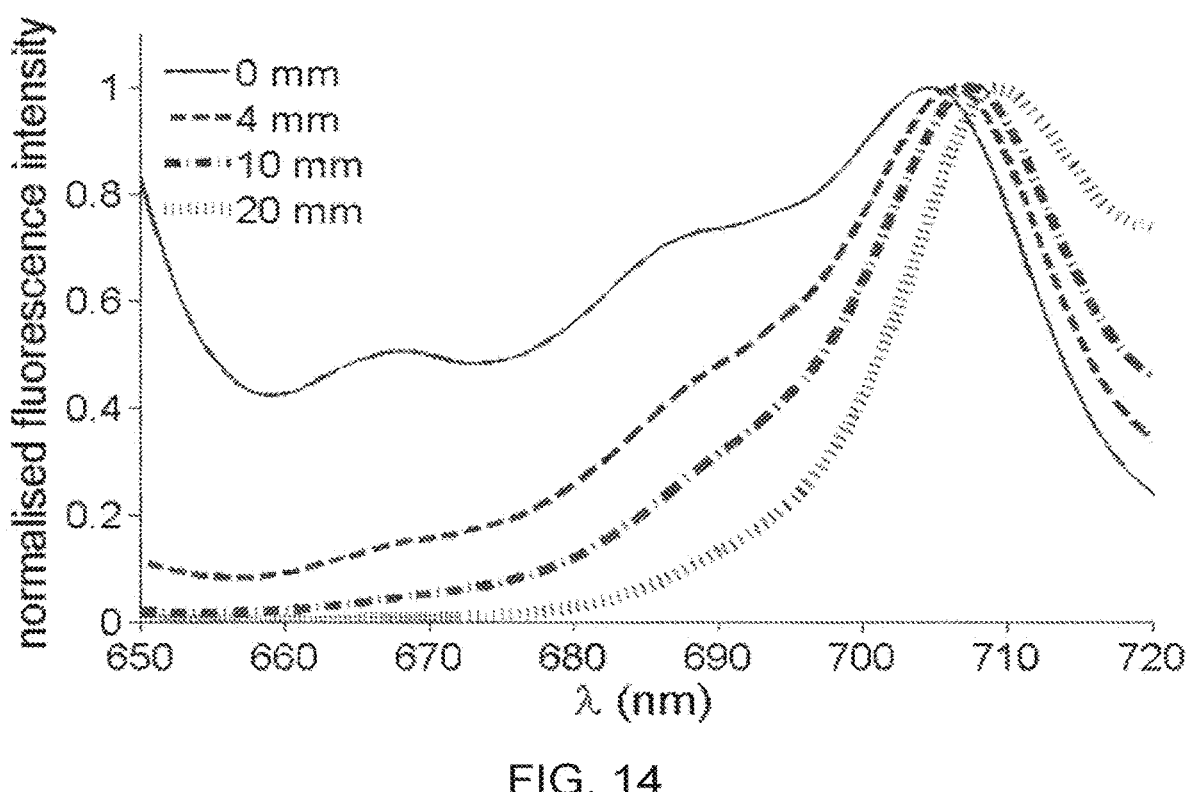
FIG. 14 illustrates spectra of fluorescent light emitted at several depths in tissue and measured above a surface of tissue.

The tomography reconstruction algorithm is based on the assumption that the received light from the tissue is diffused, resulting from scattering and absorption at each voxel in a model of the tissue. Each voxel is assigned a scattering parameter, absorption parameters for stimulus and emissions wavelengths, and fluorescence parameters, such as concentration and fluorophore lifetime. Further, it is known that an emissions spectrum of light emitted from fluorophores in tissue is distorted by passage through tissue by absorption by chromophores present in that tissue, details of the distortions induced being correlated to depth of the fluorophores in tissue as illustrated in FIG. 14. Since this distortion due to depth effectively alters a "color" of received light at the QFI, this color for each pixel of the image cube may be determined from ratios of received light intensity in each of several of the 2-D images of the image cube captured at different wavelengths near peak fluorescent emissions. For example, should spectral distortions resemble those of FIG. 14, ratios, and thus "colors", may be computed from image data acquired at multiple wavelengths in the 680 to 710 nanometer range.

Voxels external to the modeled surface contour of the tissue have absorption, scattering, and fluorescence parameters assumed to be constant, known, and zero in most cases to set boundary conditions on the model of the tissue during the process of solving the differential equations associated with light transport. Voxels within the organ, tumor, or tissue are initially assumed to scatter light and have absorbance as per an average absorption and scattering of biological tissues of the tissue type being observed. In some applications the average values of these properties are chosen based on literature values.

The model is constrained to produce image data of "colors," or ratios between light received at each of several wavelengths, of intensity matching data at selected wavelengths in the fluorescent image cube.

In this embodiment, optical diffuse tomography images of absorbance may be displayed to the surgeon, showing concentrations of chromophores in the tissue. These images may be of use during surgery in locating hidden structures such as blood vessels, aneurysms, and other concentrations of heme.

Once the absorption and scattering parameters are refined, or in embodiments displaying fluorescent parameters only a default absorption and scattering parameters may be used; for voxels within the tissue an illumination at each voxel is computed for each position of the incident beam using a computer-based light propagation model of the tissue and organ.

Next, the fluorescence concentration parameters of each voxel are computed by using a least-squares fit of the fluorescence parameters to the captured fluorescence image data. The fluorescence parameters thus computed for each voxel form a three-dimensional model of fluorophore distribution in the tissue.

A sequence of tomographic images is constructed and displayed 414 by considering intersections of a plane with fluorescence distribution of the three-dimensional model of fluorescence distribution. In an embodiment, these tomographic images are displayed on monitor 192 and/or the HUD to the surgeon as a sequence of increasing depth, the sequence being preceded by a white light photographic image of the organ or cavity for reference.

In an alternative embodiment, the tomographic images of increasing depth are encoded by coloring each image with a false color ranging from blue for images at the organ surface to red for images more than a centimeter deep into the surface. These images are then summed. The sum image, having fluorescence intensity encoded as intensity and fluorescence depth encoded as color, is then displayed on display device. White light images and images of reflected and scattered laser light may also be displayed on display device to provide the surgeon with a visual reference.

Figure 13:
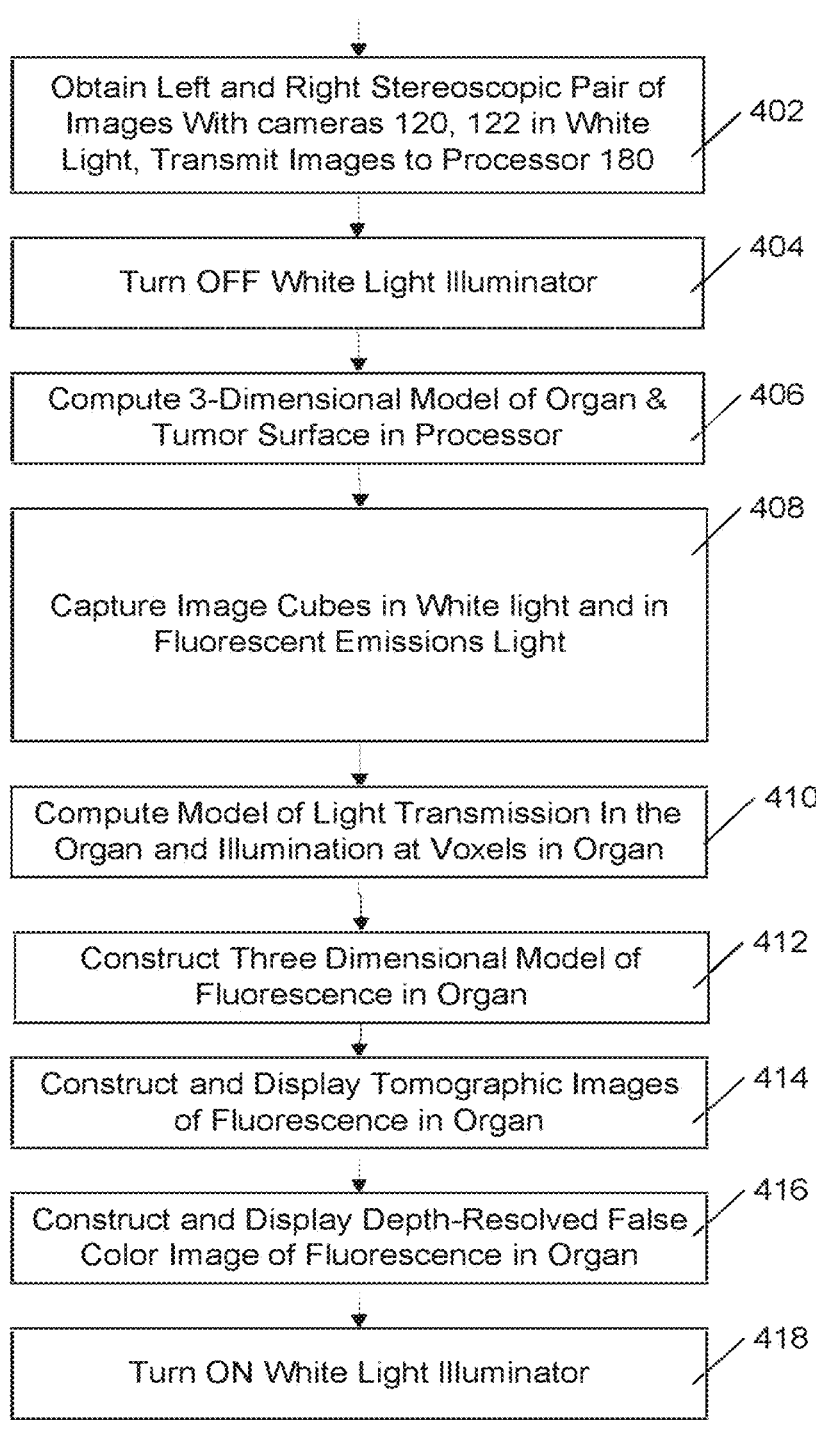
FIG. 13 is a flow chart of the method of depth resolution of fluorescence.

Once the laser scanning is complete, and while image processing proceeds, white light illuminator is turned back on. Once the surgeon studies the tomographic images on display device, the surgeon may remove additional tumor or other organ tissue and repeat the process illustrated in FIG. 13.

In an embodiment, computer simulation of the microscope shows that fluorescence of protoporphyrin IX generated by 5-ALA tagging of tumor tissue can be resolved to about two and a half millimeter resolution to a depth of twelve millimeters in organ. Further, presence of strong concentrations of protoporphyrin IX can be detected to a greater depth than that at which this resolution can be obtained.

Studies of a mouse model of glioma show that removal of protoporphyrin-IX-tagged tumor tissue detected at the surface of an operative site with a surface fluorescence microscope enhance survival; this has also been shown to be true by Stummer for human glioma. It is expected that microscope will result in both improvements in survival beyond those obtained with surface fluorescent instruments and a reduction in post-surgical neurological impairment.

It is also expected that the microscope will be of use in treating other cranial tumors such as meningioma, pituitary tumors, acoustic neuroma, and some metastatic tumors. It is expected that the microscope will also be of use in surgical treatment of tumors in other sites, including skin, breast, liver, bowel, thyroid, eyes, pancreas, kidney, bladder, prostate and muscle, as well as some lesions of other types including vascular abnormalities.

The microscope is also of use with indocyanine green for visualization of aneurismal vasculature obscured by overlying vessels, aneurysms, or other tissue.

Light as the term used herein includes electromagnetic of the visible, near ultraviolet and near infrared portions of the spectrum that may be focused with lenses and imaged with readily available semiconductor imaging devices.

While the invention has been described with reference to fluorescent substances such as indocyanine green, protoporphyrin IX, and Fluorescein, the apparatus and methods herein described are applicable to other biocompatible fluorescent prodrugs, dyes and molecules such as are known or may be developed in the future, and which may tend to concentrate in tumor tissue to a different extent than in normal tissue.

An alternative embodiment of the method uses the fluorescent tomographic microscope heretofore described to visualize a fluorescent chromophore such as may occur naturally in some types of tumor tissues. In this embodiment, there is no need to administering a prodrug or a drug. The fluorescent tomographic microscope may also be used to visualize tumors or tissues having concentrations of such a naturally occurring fluorescent chromophore that differ from concentrations in nearby normal organ stroma. Nicotinamide Adenine Dinucleotide Hydride (NADH) is an example of a naturally-occurring fluorescent chromophore that is critical to function of mitochondria. As such NADH occurs in all eukaryotic tissues, including human organ stroma and tumor tissues, but may be present at different concentrations in tumor and nearby normal stroma. Metabolically inactive tissues, such as fatty tissue of breast, may have very low concentrations of NADH, while adjacent malignant tumor tissue may be metabolically very active and therefore possess large quantities of NADH; this difference in concentration permits using the fluorescent tomographic microscope to visualize the malignant tumor tissue.

In this embodiment, scattered, reflected, and fluorescent light 1336 from organ 1306 and tumor 1344 passes through a lens of lenses 1308, a collimating optic 1338, a filter system 1340, and into a high resolution CCD camera 1342. Filter system 1340 has transparent modes for use with multiple wavelengths for imaging heme, as well as excitation-wavelength blocking and fluorescent-light passing modes for use when imaging fluorescent chromophores. In an embodiment, CCD camera 1342 is actively cooled to provide reduced noise and enhanced sensitivity to infrared light.

In operation, in a heme imaging mode, images are captured by CCD camera 1342 at each of the three wavelengths separately; these images are passed to the image processing system 232 for processing. Image processing at the first and third wavelengths is as heretofore described with reference to FIG. 22; however absorbance and scattering parameters are refined as indicated in step 1006. Image processing at the second wavelength is performed by constructing the voxel-based model of scattering and absorbance 1002 at the second wavelength, but without fluorescence parameter. The absorbance parameters at each voxel are then ratioed to provide a measure of heme oxygenation at each voxel, and summed to provide a measure of heme concentration at each voxel.

The fluorescence, heme concentration, and heme oxygenation parameters at each voxel are then mapped into tomographic image planes and displayed as tomographic images for inspection by the surgeon. The surgeon can then use these images to distinguish tumor from adjacent and nearby normal organ stroma. This embodiment is useful during surgery for visualizing below-surface heme concentrations as well as fluorescence during a wide variety of surgical procedures; and is of particular utility for distinguishing malignant breast tissue from adjacent normal breast tissue. In addition to cancer surgery, this embodiment is also useful for intraoperative identification of berry aneurisms, arteriovenous malformations, hematomas, and blood vessels.

An embodiment as heretofore described with reference to FIG. 11 is capable of imaging heme and heme oxygenation below organ surfaces in real time, and is capable of generating an additional tomographic image indicating changes in heme concentration and/or heme oxygenation. These images indicating changes in heme concentration and oxygenation are useful for functional neuroimaging to confirm identification of foci of seizure activity because neural activity depletes oxygen and increases blood flow. Precise identification of foci of seizure activity is of importance during surgical procedures intended to alleviate epilepsy, and such surgery is occasionally done under local anesthesia to permit identification of such foci. Since the apparatus can identify changes in heme concentration and oxygenation over a centimeter below a surface, this embodiment may also be used for functional neuroimaging through the intact skull, although resolution is less than that available with the skull open.

In an alternative embodiment, fluorescence excitation of fluorophores in tissue is performed using a broad-beam source in the NIR at the excitation wavelength, $\lambda_{ex}$. It has been found that fluorescent light emitted by concentrations of fluorophores like protoporphyrin IX is more strongly absorbed by tissue in the 650-670 nanometer wavelength range than in longer wavelengths such as near 700-710 nanometers, and that with proper stimulus radiation, proto-porphyrin IX will emit radiation having wavelengths from 650 to 720 nanometers. Similar effects may also occur with fluorescent light emitted by other fluorophores at similar or other wavelengths. This effect is due to the presence in tissue of chromophores, substances-including hemoglobin—in tissue that absorb or scatter light more intensely at some wavelengths than others. Typically, though, while fluorescent radiation is emitted across this range, the emitted radiation is not uniform in intensity across the wavelength band.

FIG. 14 illustrates spectra of fluorescent radiation emitted by fluorophores at several depths in tissue as observed above the tissue. These spectra have been normalized to the same peak level. A first spectrum is that of fluorophores at the surface of the tissue, and is close to the spectra of light as emitted by the fluorophores themselves. A second spectrum is that of light from fluorophores four millimeters below the surface as seen from above the surface, a third spectrum is that of light from fluorophores one centimeter below the surface as seen from above the surface, and a fourth spectrum is that of light from fluorophores two centimeters below the surface as observed from above the surface.

In an embodiment for use with the prodrug 5-ALA and the fluorophore protoporphyrin-IX, emitted fluorescence signals are measured at two wavelengths, $\lambda_{1,2}$, each of which is longer than the excitation wavelength $\lambda_{ex}$, using band-pass filters and a cooled CCD camera; in other embodiments emitted fluorescence signals are measured at multiple, meaning three or more, wavelengths using appropriate band-pass filters having center pass-band wavelengths at different wavelengths in the range of 650-720 nanometers. For example, if tissue has absorption and scattering character-istics similar to the tissue assumed in FIG. 27, and fluores-cent light intensity I1 is measured through a filter having bandpass 1610 between 680 and 690 nanometers while a fluorescent light intensity I2 is measured through a filter having bandpass 1612 between 700 and 710, a ratio of I1 to I2 will be considerably smaller when the fluorophore is two centimeters below the surface than when the fluorophore is at the surface of the tissue.

Embodiments for use with other fluorophores than pro-toporphyrin IX will require different calibration tables and may operate at wavelengths other than those specified in the previous paragraph. Further, it is known that optical absorp-tion and scattering characteristics differ from one type of tissue to another, and may also change somewhat with time as a subject's oxygenation levels change during surgery. In order to provide for this variability, an embodiment, has a library with normal optical characteristics of a variety of tissue types that the fluorescent tomographic microscope is expected to encounter during surgery. For example, the library may contain optical characteristics for normal brain grey matter and for normal brain white matter when the microscope is used during removal of brain tumors such as gliomas. An operator then selects the appropriate tissue type for tissue in the field of view, and optical characteristics of that tissue type are then used for computation of fluorophore depth and distribution.

In an alternative embodiment, library has optical charac-teristics of a variety of tissue types with each tissue type measured under different levels of oxygenation. In these embodiments, the operator measures tissue oxygenation with direct or optical techniques and optical characteristics of the tissue are determined based on both tissue oxygen-ation and tissue type.

Assuming that tissue absorption due to the fluorophore concentrations of tumor is much smaller than absorption by other chromophores of tissue, the light signals at each emission wavelength can be modeled using the expression $$\psi^{em}\left(\vec{R}, \lambda^{ex}, \lambda\right) \approx Q_F \varepsilon_F^{em}(\lambda) \int_\Omega d^3 r \psi^{ex}(\vec{r}) C_F(\vec{r}) G^{em}\left(\vec{R}, \vec{r}, \delta^\lambda, D^\lambda\right) \qquad \text{(Eq. 8)}$$

where $\vec{R}$ is the vector corresponding to the detection point on the tissue surface, which is mapped onto a pixel or sub-ensemble of pixels on the CCD chip. $Q_F$ is the quantum yield, $\varepsilon_F^{em}(\lambda)$ the emission spectrum and $C_F(\vec{r})$ the con-centration of fluorescent molecules at location $\vec{r}$, where $\vec{r}$ is an arbitrary vector corresponding to the location of a point inside the interrogated tissue. In Eq. (8), light transport is modeled as a diffusive process. The fluence function $\psi^{ex}$ is the excitation light field, and $G^{em}$ is the diffusion equation Green's function, which corresponds to the radiant exposure in response to a light impulse at $\vec{r}$. For boundary conditions associated with an infinite homogenous medium, it is given by $$G_\infty^{em}(\vec{R}, \vec{r}, \delta^\lambda, D^\lambda) = \frac{\exp(-|\vec{R} - \vec{r}|/\delta^\lambda)}{4\pi D^\lambda |\vec{R} - \vec{r}|}, \qquad \text{(Eq. 9)}$$

where the diffusion constant is $D^\lambda = 1/3$ $(\mu_\alpha^\lambda + \mu_s'^\lambda)$ and the penetration depth is $$\delta^\lambda = \sqrt{D^\lambda / \mu_a^\lambda}.$$

$\mu_a^\lambda$ is the absorption coefficient of the tissue while $\mu_s'^\lambda$ is the reduced scattering coefficient.

A closed form expression is derived from Eq. (8) and Eq. (9), from which a depth value can be estimated for each point imaged on the tissue surface, using an approximation that all fluorescence emitted from the surface is from a point-like distribution of fluorophore with molar concentra-tion $C_F$ location at position $r_s$. This is equivalent to setting $C_F(\vec{r}) = C_F \delta^{(3)}(\vec{r} - \vec{r}_s)$ in Eq. (8), which then takes the form $$\psi^{em}\left(\vec{R}, \lambda^{ex}, \lambda\right) \approx C_F Q_F \varepsilon_F^{em}(\lambda) \psi^{ex}(\vec{r}_s) G^{em}\left(\left|\vec{R} - \vec{r}_s\right|, \delta^\lambda, D^\lambda\right) \qquad \text{(Eq. 10)}$$

where the depth of the distribution is $|\vec{R} - \vec{r}_s| = d$ assuming that the detection point $\vec{R}$ is located directly above the source of fluorescence at $r_s$.

To illustrate how fluorescence spectra are affected by varying the depth of the fluorophore distribution, see FIG. 27 for protoporphyrin-IX spectra computed with Eq. (10) for depths varying up to d=20 mm for an anticipated typical absorption spectrum labeled and a constant value of reduced scattering ($\mu_s' = 1$ mm$^{-1}$). As the object gets deeper in the tissue, the optical properties of the tissue demonstrate an increasing influence on shaping the observed spectrum because of the increasing lightpaths traversed by light. The information contained in the distorted spectra may be distilled into a single quantity by calculating the ratio of the signal at two emission wavelengths, $$\Gamma = \frac{\psi^{em}\left(\vec{R}, \lambda^{ex}, \lambda_1\right)}{\psi^{em}\left(\vec{R}, \lambda^{ex}, \lambda_2\right)} \times \frac{\varepsilon_F^{em}(\lambda_2)}{\varepsilon_F^{em}(\lambda_1)} = \frac{G^{em}\left(\vec{R}, \vec{r}_s, \delta^{\lambda_1}, D^{\lambda_1}\right)}{G^{em}\left(\vec{R}, \vec{r}_s, \delta^{\lambda_2}, D^{\lambda_2}\right)} \qquad \text{(Eq. 11)}$$

where the intensity values at each wavelength are normalized with the relative signal strength of an undistorted emission spectrum, implying that $\Gamma$ should be equal to 1 for d=0 mm.

In Eq. (11), $\Gamma$ is independent of the diffuse excitation field. This means that, in the point-source approximation limit, the ratio is independent of scattering and absorption of the stimulus light.

Inserting Eq. (9) into Eq. (11), we find that the logarithm of the fluorescence ratio for an infinite medium is linearly related to the depth in tissue of the fluorophores with a slope equal to the difference in penetration depth between wavelengths $\lambda_1$ and $\lambda_2$, This linear relationship can potentially be used in estimating depth from a simple measured ratio in the case of diffusive medium of infinite spatial extent. A more realistic model for epi-illumination imaging may also be obtained assuming there is an index of refraction mismatch boundary between tissue and air. The relationship obtained is then similar—up to a multiplicative factor—for depth values larger than approximately two millimeters. For smaller values than two millimeters, the relationship is non-linear.

An alternative embodiment superficially resembling that of FIG. 11 as heretofore described constructs a fluorescence image cube having images taken at a different center wavelength in the range of wavelengths emitted by a typical fluorescent material such as protoporphyrin IX, such as in the range 650-720 nanometers.

As described above with reference to Equations (8-11), the spectra of fluorescent light passing through tissue is altered by absorption and scattering in the tissue, such that spectra of the received fluorescent light encodes depth information. In an embodiment, two bandpass elements are used to derive a spectral deformation and depth for the fluorescent light captured in each pixel; in an alternative embodiment, three or more bandpass elements are used to more precisely estimate spectral deformation due to passage of emitted light through tissue and thereby estimate depth for each pixel of the image.

In an embodiment, the depth information determined as described above, using modeling of incident laser light and depth information derived from spectral information in received fluorescent light, are used to provide a refined depth information, and to thereby provide a refined model of the tumor. In an alternative mode of operating this embodiment, the scanning laser may be disabled and depth information derived solely from spectral deformation of fluorescent light stimulated by an appropriate flood illuminator.

In an embodiment using two image planes from the image cube in the wavelength range of fluorescence in the fluorophores in tumor, a two dimensional table is used. This table is generated according to the optical properties of the tissue at the wavelengths of the bandpass filters as determined by measurement through imaging of scattering of a beam, or from a library of optical properties as previously discussed herein. This table is indexed by intensity at the higher wavelength bandpass filter in X, and intensity in the lower wavelength bandpass filter in Y, the table having entries of approximate depth of tumor based upon differences between intensity of fluorescent light passing the higher wavelength filter and the lower wavelength filter. The table is precomputed and stored in memory of the image processor to permit fast access. Intensity from each pixel in high wavelength and low wavelength images are used with a table interpolation algorithm as known in the art of computing to derive a depth associated with each pixel, and a three-dimensional model of fluorophore distribution is computed. Information from the model of fluorophore distribution is then displayed to the surgeon; this may be in the form of tomographic images, a topographic map, or by color coding of fluorescence magnitude with determined depth.

In another embodiment, the optical properties of the tissue as determined above at the wavelengths of the bandpass filter elements is used to compute the 'slope' for the log-linear relationship of the ratio of intensity at two wavelengths as described above with reference to substitution of Eq. (9) into Eq. (11). This 'slope' allows us to relate the depth in tissue of the fluorophores to the difference in intensity between wavelengths $\lambda_1$ and $\lambda_2$. Then, the depth can be estimated based on the measured ratio:

$$d = \frac{\ln \Gamma - \ln \dfrac{D^{\lambda_2}}{D^{\lambda_1}}}{-\left[\dfrac{1}{\delta^{\lambda_1}} - \dfrac{1}{\delta^{\lambda_2}}\right]}, \qquad \text{(Eq. 12)}$$

Alternatively the more general expression associated with a semi-infinite diffusive medium may be used, as described above with reference to Eq. (8-10).

Hyperspectral Imaging System Look-Up Table (LUT) Approach for Estimation of Tissue Optical Properties The hyperspectral imaging system with white-light illumination can be used to estimate the tissue optical properties across the full field of view to create maps of tissue optical properties, such as absorption ($\mu a$) and reduced scattering ($\mu s'$) coefficients. An embodiment of this method uses a look-up table (LUT), which has of a set of basis functions of spectrally resolved diffuse reflectance including reflectance ($Rd(\lambda)$) at known absorption ($\mu a(\lambda)$) and scattering ($\mu s'(\lambda)$). In a particular embodiment, the table is indexed by at least reflectance Rd, and wavelength $\lambda$, the components of reflectance spectra; and contains multiple spectra, each captured at different values of known absorption and scattering. The table has values recorded therein for absorption $\mu a$, and scattering $\mu s'$ at each table spectra. Captured spectra measured at each pixel, which includes reflectance at a number of different wavelengths, are fit to determine at least the closest table entries, and absorption and scattering parameters are read from the table. In order to conserve table space while providing adequate accuracy, lookups into the table for absorption and scattering parameters are interpolated using an interpolation method selected from the group of linear, cubic, or spline interpolation functions.

First, diffuse reflectance spectra, $Rd(\lambda)$, are measured in phantoms of known and varying optical absorption, $\mu a$, and reduced scattering, $\mu s'$, across a range of values typically found in human tissues, including both normal tissues and pathological tissues such as tumor. The collected $Rd(\lambda)$ at known $\mu a(\lambda)$ and $\mu s'(\lambda)$ are used to create a 4-dimensional set of basis functions [Rd, $\lambda$, $\mu a$, $\mu s'$]. Wide-field spectrally-resolved reflectance images of tissue of unknown tissue optical properties, e.g., acquired during surgery, are then decomposed into Rd at each pixel. In an alternative embodiment, regularized minimization is applied to fit the basis functions to observed $Rd(\lambda)$ at each pixel such that a best fit to a weighted sum of the basis functions matches Rd. The fitted basis functions yield estimates of $\mu a(\lambda)$ and $\mu s'(\lambda)$ at every pixel.

In particular embodiments, the estimated absorption and reduced scattering coefficients, $\mu a(\lambda)$ and $\mu s'(\lambda)$ are also used to determine additional quantitative biomarkers that include but are not limited to hemoglobin concentration and oxygen saturation.

This technique enables a hyperspectral imaging system to collect diffuse reflectance data, and apply a minimization algorithm unto a set of known basis functions, (in a particular example using the lookup table described above) to make explicit estimates of tissue optical properties across the full field of view.

Hyperspectral Quantitative Fluorescence Imaging (qFI) Using a Look-Up Table (LUT) for Estimation of Tissue Optical Properties and a Light Transport Model The hyperspectral imaging system with white-light illumination and fluorescence excitation light (e.g., light at 405 nm for PpIX) can be used to perform quantitative fluorescence imaging using a LUT and light transport model approach. In this embodiment, the estimates of $\mu a(\lambda)$ and $\mu s'(\lambda)$ determined by fitting spectra to entries of the table, and looking up $\mu a(\lambda)$ and $\mu s'(\lambda)$ in the lookup table at every pixel m are used to create a 'correction image'. The 'correction image' is then used to correct the measured raw fluorescence based on a light transport model, such as the light transport model of Eq. 13 below, to produce corrected quantitative fluorescence images. This light transport model of Eq. 13 is derived from a model published as Kim, A., et al., *Quantification of in vivo fluorescence decoupled from the effects of tissue optical properties using fiber-optic spectroscopy measurements*, J Biomed Opt 15, 067006 (2010), the disclosure of which is incorporated herein by reference.

$$f_{x,m} = \left(\frac{\mu_{a,x}}{1 - R_{t,x}}\right)\left(\frac{F_{x,m}}{R_m}\right) \tag{Eq. 13}$$

$$R_{t,x} = \frac{a'_x}{1 + 2\kappa(1 - a'_x) + \left[1 + (2\kappa/3)\right]\sqrt{3(1 - a'_x)}} \tag{Eq. 14}$$

where $R_{t,x}$ is the total diffuse reflectance. This parameter depends on the internal reflectance parameter K and the reduced albedo, $\alpha'_x$, which in turn are defined as:

$$\kappa = \frac{(1 + r_{id})}{(1 - r_{id})} \tag{Eq. 15}$$

-continued $$a'_x = \frac{\mu'_{s,x}}{\mu_{a,x} + \mu'_{s,x}} \tag{Eq. 16}$$

With $r_{id} = -1.44n_{rel}{-2} + 0.71n_{rel}{-1} + 0.67 + 0.0636n_{rel}$, where $n_{rel} = n_{tissue}/n_{external}$ for matching internal and external refractive indexes K=1.

$\mu_{a,x}$ is the absorption coefficient at the excitation wavelength (e.g., if using PpIX as the fluorophore, $\lambda$=405 nm);

$F_{x,m}$ is the raw (uncorrected) fluorescence emissions; and $R_m$ is the diffuse reflectance at the emission wavelength.

Spectral unmixing (e.g., least squares approach) is then used to separate the contributions from the fluorophore(s) being imaged, which may include PpIX and tissue autofluorescence, to construct a full-field of view image of fluorophore(s) concentrations, such as a PpIX concentration map. This method enables quantitative fluorescence imaging qFI by correcting the raw fluorescence using explicit estimates of the tissue optical properties at the fluorescence wavelength and stimulus wavelength to create a 'correction image' to apply a light transport model of quantitative fluorescence. The fluorescence model presented here assumes that the optical absorption at the excitation wavelength hx is high relative to that at the emission wavelength, and as such, most fluorophore absorption occurs close to the excitation light source. The model assumes that fluorescence migration paths are approximate by those of the reflectance photons at the emission wavelength.

Figure 15:
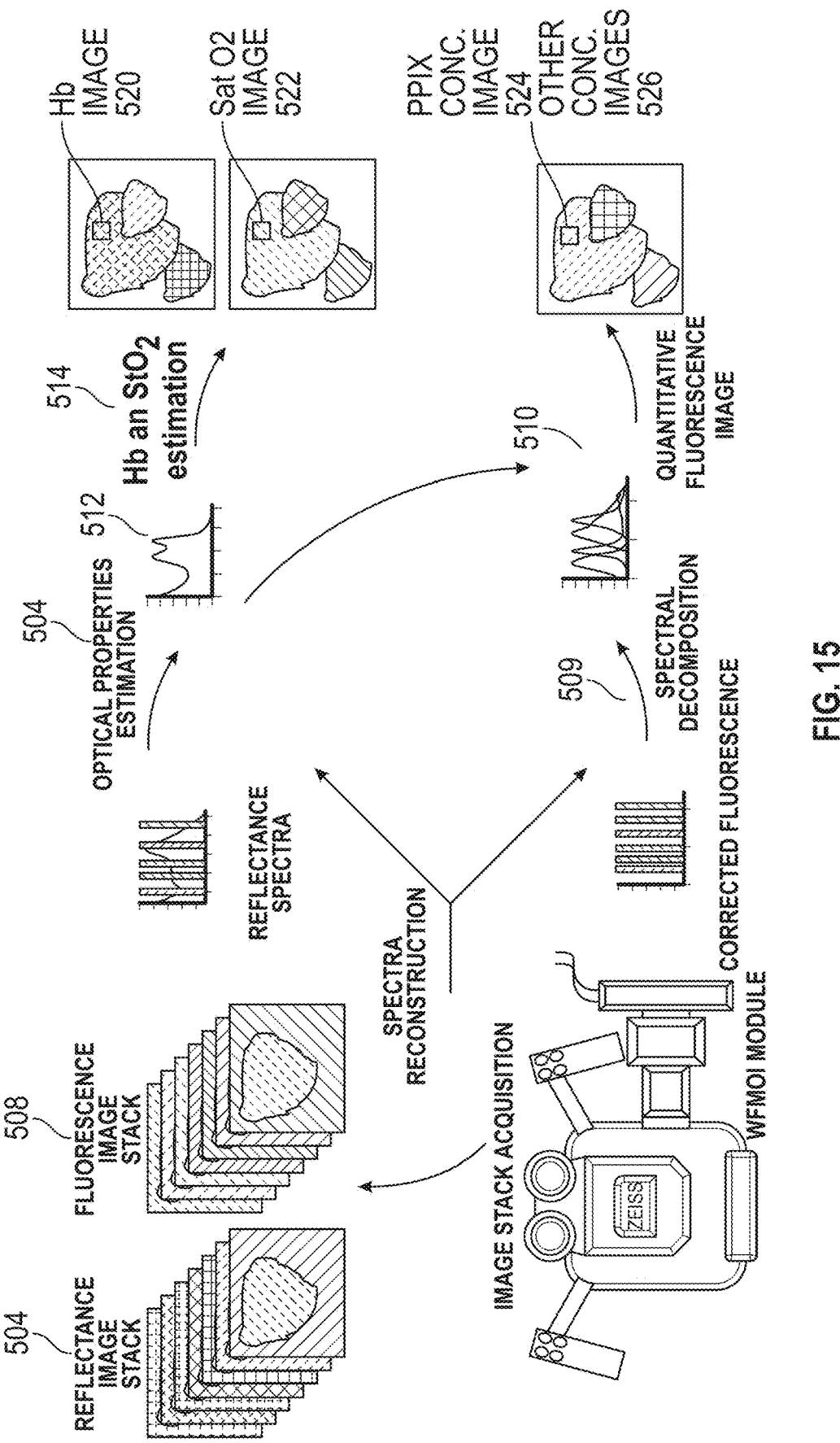
FIG. 15 is a flow diagram of a method of imaging.

In an embodiment, FIG. 15 is a flow diagram of a method of imaging.

FIG. 16 is a flowchart of obtaining and correcting a fluorescence image for absorption and scattering in a target, such as tissue, in order to quantify fluorescence and reflectance spectrally-derived images of the tissue. With reference to FIGS. 15 and 16, and FIG. 11, white light is provided 502 to the target, or tissue, 152 by illuminators 166; and light from the target is imaged 504 by camera through a tunable optical filter of the target while tuning the filter to a plurality of wavelengths, the series of images forming a spectral image; providing a stimulus light to the target 506 using illuminators 168; and taking a fluorescence emission image of the target 508 through filters tuned to block stimulus light. In an optional step 509 the fluorescence emission images of target 508 are captured as fluorescence spectra by sweeping the tunable optical filter and capturing multiple images of the target, the fluorescence spectra are then decomposed 509 to provide individual fluorescence images related to each of several fluorophores expected to be present in the target.

The images are then processed to determine absorption and scattering spectral parameters; in an embodiment determining the absorption and scattering parameters is performed by interpolating in the table as previously described. The fluorescence emission image or images are then corrected 510 by using the absorption and scattering parameters to produce corrected fluorescence emission images giving a quantitative distribution of each fluorophore, such as PPIX 524 and other fluorophores 526 that may be native to the tissue or administered to a patient.

The absorption and scattering parameter spectra at each pixel are then decomposed 512 to provide tissue component images mapping concentrations of typical tissue constituents such as oxygenated and deoxygenated hemoglobin; these are then added and ratioed 514 to provide a total hemoglobin image 520 and a percent-oxygenation 522 map or image of hemoglobin oxygenation in the tissue. The images, including corrected, quantitative, fluorescence, hemoglobin, and percent oxygenation, are then displayed 516 for use in diagnosis.

Combinations

Various combinations of the elements may occur in a practical system. For example, in embodiments, optical system may be a surgical microscope, while in other embodiments other optical systems having the ability to illuminate with stimulus or white light, and to image in white or stimulus light and then in fluorescence emitted light may be used. In particular embodiments, the following combinations of features are anticipated:

An imaging system designated A, having an illumination device for illuminating a target, the illumination device adapted to selectively emit a white light and a fluorescent stimulus light; a device for receiving light from the target, the device for receiving light comprising at least one optical output port at which at least a portion of the received light is provided as an output; a tunable filter for receiving the portion of the received light provided as the output from the device for receiving light, the tunable filter being tunable to pass a filtered portion of the received light, the filtered portion of the received light having a plurality of wavelengths selected by the tunable filter; a high-resolution, broad-bandwidth electronic camera for receiving the light of a plurality of wavelengths selected by the tunable filter and encoding a plurality of electronic images therefrom, the electronic images representing spectra at pixels of the images; and a processor configured to process the plurality of electronic images to form an image of the target; wherein the image includes an image of fluorescent emissions by any fluorophore in the target.

It is understood that the system described in A is adapted for use with a target of human or other mammalian tissue.

An imaging system designated AB including the imaging system designated A wherein the device for receiving light is a surgical microscope.

An imaging system designated AC including the imaging system designated A or AB, wherein at least some of the electronic images the processor is configured to process are generated from fluorescence light received by the surgical microscope and wherein at least some of the electronic images processed by the processor are generated from reflectance light received by the surgical microscope.

An imaging system designated AD including the imaging system designated A, AB, or AC, wherein, in forming the image of the target, the processor is configured to use the electronic images generated from reflectance light to compensate the electronic images from the fluorescence light for absorption and scattering while generating the image of fluorescent emissions from the target.

An imaging system designated AE including the imaging system designated AD wherein the processor is configured to determine absorption and a scattering parameter at each pixel while compensating the electronic images from the fluorescence light for absorption and scattering.

An imaging system designated AF including the imaging system designated AE wherein a table interpolation is used to determine an optical absorption and a scattering parameter at each pixel.

An imaging system designated AG including the imaging system designated A, AB, AC, AD, AE, or AF, wherein the tunable filter is a liquid crystal tunable filter.

The system designated AG or AH wherein a fluorophore in the target comprises protoporphyrin IX.

An imaging system designated AH including the imaging system designated A, AB, AC, AD, AE, or AF wherein the tunable filter is an acousto-optic tunable filter.

A surgical microscope system designated B, including: an illumination device for illuminating a target, the illumination device adapted for selectively emitting a fluorescent stimulus light and a white light; at least one optical output port at which at least a portion of received light received from the target is provided; a tunable filter for receiving the portion of the received light, the tunable filter being tunable to pass a filtered portion of the received light, the filtered portion of the received light having a plurality of wavelengths selected by the tunable filter and provided as output from the tunable filter; an electronic camera for receiving the light of a plurality of wavelengths selected by the tunable filter, the electronic camera adapted to convert the light selected by the tunable filter to a plurality of electronic images while the tunable filter is tuned; and a processor configured to process the plurality of electronic images to form images of the target, wherein the images of the target comprise images of fluorophores in the target.

A surgical microscope system designated BA including the system designated B, wherein the electronic images the processor is configured to process include images generated from fluorescence light received from the target and images generated from reflectance light received from the target.

A surgical microscope system designated BB including the system designated B or BA, wherein, in forming the images of the target, the processor uses the images generated from reflectance light to compensate the images generated from the fluorescence light for absorption and scattering in the target.

A surgical microscope system designated BC including the system designated B, BA, or BB, wherein the tunable filter is selected from the group consisting of a liquid crystal tunable filter and an acousto-optic tunable filter.

A method of imaging designated C including providing a white light to a target; taking a series of images through a tunable optical filter of the target while tuning the filter to a plurality of wavelengths, the series of images forming a spectral image; providing a stimulus light to the target; taking a fluorescence emission image of the target; processing the spectral image to determine an absorption and a scattering parameter at pixels of the images; and correcting the fluorescence emission image using the absorption and scattering parameters to produce a corrected fluorescence emission image.

A method designated CA including the method designated C further including decomposing the spectral image to provide images of components of the target, the components including specific scattering and absorbing substances expected to be in the target.

A method designated CB including the method designated CA wherein the target comprises tissue, and wherein the components of the target include oxygenated and deoxygenated hemoglobin.

The method designated CB wherein the images of components of the target are combined to form images of total hemoglobin and hemoglobin oxygen saturation.

A method of imaging designated D including providing a white light to a target; taking a series of images through a tunable optical filter of the target while tuning the filter to a plurality of wavelengths, the series of images forming a spectral image; processing the spectral image to determine an absorption and a scattering parameter at pixels of the images; and decomposing the spectral image to provide images of components of the target, the components including specific scattering and absorbing substances expected to be in the target.

A method designated DA including the method designated D wherein the target comprises tissue, and wherein the components of the target include oxygenated and deoxygenated hemoglobin.

The method of claim DA wherein the images of components of the target are combined to form images of total hemoglobin and hemoglobin oxygen saturation.

While the invention has been particularly shown and described with reference to a preferred embodiment thereof, it will be understood by those skilled in the art that various other changes in the form and details may be made without departing from the spirit and scope of the invention. It is to be understood that various changes may be made in adapting the invention to different embodiments without departing from the broader inventive concepts disclosed herein and comprehended by the claims that follow.

What is claimed is:

1. A hyperspectral imaging system for determining depth and concentration of fluorophores in tissue of a patient, comprising:
   a configurable illuminator adapted to illuminate the tissue with light selected from the group consisting of white light and fluorescence stimulus light;
   a hyperspectral camera configurable to capture a white-light hyperspectral image cube of the tissue as illuminated with white light from the configurable illuminator, the hyperspectral camera configured to pass light from the tissue through a tunable filter into an electronic camera;
   the hyperspectral camera also configurable to capture a fluorescence-light hyperspectral image cube of the tissue as illuminated with fluorescence stimulus light from the configurable illuminator;
   an image processor configured by processing routines in memory to:
      analyze spectral bands of pixels of the white-light hyperspectral image cube near a wavelength of the fluorescence stimulus light and a wavelength of associated fluorescence emissions to extract scattering and absorption parameters at pixels of the tissue at the wavelengths of the fluorescence stimulus light and the associated fluorescence emissions;
      normalize at least one selected pair of images of the fluorescence-light hyperspectral image cube, the at least one selected pair of images being associated with two different respective wavelengths near a peak wavelength of the fluorescence emissions,
      derive, based upon the scattering and absorption parameters, depth of the fluorophores in the tissue at pixels of the at least one selected pair of images from a ratio between the images of the at least one selected pair of images of the fluorescence-light hyperspectral image cube, as normalized;
      determine fluorophore concentration at voxels of a voxel-based model using the extracted scattering and absorption parameters derived from the white-light hyperspectral image cube, the depth of the fluorophores at the pixels, and at least one image of the fluorescence-light hyperspectral image cube; and
      perform tissue deformation modeling to determine tumor shift during surgery.

2. The hyperspectral imaging system of claim 1, where the tissue deformation modeling is configured to be performed using a stereo-optical surface model extracted from stereo images of the tissue captured by stereo cameras.

3. The hyperspectral imaging system of claim 2 wherein the memory is configured with routines to perform extraction of the stereo-optical surface model, and the memory is further configured with routines for preparing images for display through a display interface or for communicating through a network interface to a server to include information derived from a patient's preoperative MRI scans, preoperative CAT scans, or both preoperative MRI and CAT scans.

4. The hyperspectral imaging system of claim 3 wherein the tissue is brain tissue.

5. The hyperspectral imaging system of claim 2 wherein the image processor is configured to, when analyzing spectral bands of pixels to extract scattering and absorption parameters, perform steps comprising setting up the voxel-based model with the scattering and absorption parameters and refining the scattering and absorption parameters.

6. The hyperspectral imaging system of claim 5, wherein the image processor is configured to, when normalizing at least one selected pair of images of the fluorescence-light hyperspectral image cube, to select a plurality of pairs of images of the fluorescent light image cube; and when deriving, collectively evaluating a plurality of ratios, each obtained from a respective one of the plurality of pairs.

7. The hyperspectral imaging system of claim 5, wherein the image processor is configured to fit, to the ratio between the images, a model of depth-dependent spectral properties of fluorescence emissions, to determine the depth of the fluorophores and, prior to fitting, determine parameters of the model of the depth-dependent spectral properties from the scattering and absorption parameters.

8. The hyperspectral imaging system of claim 5, the image processor configured to, when normalizing, divide each intensity of pixels of images in the at least a subset of the fluorescence-light hyperspectral image cube by (a) intensity of pixels signal in an image of the white-light hyperspectral image cube corresponding to wavelength of the fluorescence stimulus light and (b) a power of signal intensity of pixels in an image of the white-light hyperspectral image cube associated with same wavelength as the respective image in the at least a subset of the fluorescence-light hyperspectral image cube.

9. The hyperspectral imaging system of claim 1 further comprising a probe coupled to a spectrophotometric detector adapted to receive light from a single point on the tissue of the patient;
   wherein the image processor is further configured by the processing routines to:
      use the probe to analyze optical biomarkers in the tissue.

10. The system of claim 9 wherein the probe is coupled to the illuminator.

11. The system of claim 9 wherein the biomarkers include fluorophore concentrations, oxygen saturation, and hemoglobin concentration.

12. A hyperspectral imaging system for determining depth and concentration of fluorophores in tissue of a patient, comprising:
   a hyperspectral camera configurable to capture a white light hyperspectral image cube of the tissue as illuminated with white light, the hyperspectral imaging camera including a tunable filter and a broad-spectrum electronic camera;

the hyperspectral camera also configurable to capture a fluorescence-light hyperspectral image cube of the tissue as illuminated with fluorescence stimulus light;

an image processor coupled to receive the white light hyperspectral image cube and the fluorescence-light hyperspectral image cube and configured to:

analyze spectral bands of the white light hyperspectral image cube near a wavelength of the fluorescence stimulus light and a wavelength of associated fluorescence emissions to extract at pixels scattering and absorption parameters of the tissue at the wavelengths of the fluorescence stimulus light and the associated fluorescence emissions;

normalize at least one selected pair of images of the fluorescence-light hyperspectral image cube, the at least one selected pair of images being associated with two different respective wavelengths near a peak wavelength of the fluorescence emission;

derive, the depth of the fluorophores in the tissue at pixels based upon the scattering and absorption parameters and a ratio between two images of the at least one selected pair of images of the fluorescence-light hyperspectral image cube, as normalized;

determine fluorophore concentration at voxels of a voxel-based model using the extracted scattering and absorption parameters derived from the white-light hyperspectral image cube, and the depth at pixels of the fluorophores at pixels and at least one image of the fluorescence-light hyperspectral image cube; and perform tissue deformation modeling to determine tumor shift during surgery.

13. The hyperspectral imaging system of claim 12 where the tissue deformation modeling is configured to be performed using a stereo-optical surface model extracted from stereo images of the tissue captured by stereo cameras.

14. The hyperspectral imaging of claim 13 wherein the memory is configured with routines to perform extraction of the stereo-optical surface model, and the memory is further configured with routines for preparing images for display through a display interface or for communicating through a network interface to a server to include information derived from a patient's preoperative MRI scans, preoperative CAT scans, or both preoperative MRI and CAT scans.

15. The hyperspectral imaging system of claim 13 wherein the tissue is brain tissue.

16. The hyperspectral imaging system of claim 13, the image processor configured to, while deriving the depth of fluorophores in the tissue, compare a ratio of two images of the at least one selected pair of images to a model of depth-dependent spectral properties of the ratio of two images of the at least one selected pair of images.

17. The hyperspectral imaging system of claim 16, wherein the image processor is configured to, prior to comparing the ratio between the two images of the at least one selected pair of images, determine parameters of the model of the depth-dependent spectral properties from the scattering and absorption parameters.

18. The hyperspectral imaging system of claim 16, the model specifying the depth as $d=[\ln(\Gamma)-\ln(D\_ID\_2)]/[1/(\delta\_2-1/\delta\_1)]$, wherein (a) $D\_1$ and $D\_2$ are diffusion constants for the two different wavelengths, respectively, (b) $\delta\_1$ and $\delta\_2$ are penetration depths for the two different wavelengths, respectively, and (c) $\Gamma$ is the ratio, the processor further configured to determine each of $D\_1$, $D\_2$, $\delta\_1$, and $\delta\_2$ from the scattering and absorption parameters.

19. The hyperspectral imaging system of claim 16, wherein the white-light hyperspectral image cube and the fluorescence-light hyperspectral image cube are captured at a same set of wavelengths, and wherein the image processor is configured to, when normalizing, correct at least two pairs of images of the fluorescence-light hyperspectral image cube.

20. A hyperspectral imaging system for determining depth and concentration of fluorophores in tissue of a patient, comprising:

a configurable illuminator adapted to illuminate the tissue with light selected from the group consisting of white light and fluorescence stimulus light;

a probe coupled to a spectrophotometric detector adapted to receive light from a single point on the tissue of the patient a hyperspectral camera configurable to capture a white-light hyperspectral image cube of the tissue as illuminated with white light from the configurable illuminator;

the hyperspectral camera also configurable to capture a fluorescence-light hyperspectral image cube of the tissue as illuminated with fluorescence stimulus light from the configurable illuminator;

an image processor being configured by processing routines in memory to:

analyze spectral bands of pixels of the white-light hyperspectral image cube near a wavelength of the fluorescence stimulus light and a wavelength of associated fluorescence emissions to extract scattering and absorption parameters at pixels of the tissue at the wavelengths of the fluorescence stimulus light and the associated fluorescence emissions, normalize at least one selected pair of images of the fluorescence-light hyperspectral image cube, the at least one selected pair of images being associated with two different respective wavelengths near a peak wavelength of the fluorescence emissions, derive, based upon the scattering and absorption parameters, depth of the fluorophores in the tissue at pixels of the at least one selected pair of images from a ratio between the images of the at least one selected pair of images of the fluorescence-light hyperspectral image cube, as normalized;

determine fluorophore concentration at voxels of a voxel-based model using the extracted scattering and absorption parameters derived from the white-light hyperspectral image cube, the depth of the fluorophores at the pixels, and at least one image of the fluorescence-light hyperspectral image cube, and use the probe to analyze optical biomarkers in the tissue.

21. The system of claim 20 wherein the probe is coupled to the illuminator.

22. The system of claim 20 wherein the optical biomarkers include fluorophore concentrations, oxygen saturation, and hemoglobin concentration.

\* \* \* \* \*